US011352616B2

(12) United States Patent
Cho et al.

(10) Patent No.: US 11,352,616 B2
(45) Date of Patent: Jun. 7, 2022

(54) NANOSTRUCTURE FOR DETECTING CELL-FREE DNA USING CONDUCTIVE POLYMER AND THE USE THEREOF

(71) Applicant: NATIONAL CANCER CENTER, Goyang-si (KR)

(72) Inventors: Youngnam Cho, Goyang-si (KR); Eun Sook Lee, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 16/229,772

(22) Filed: Dec. 21, 2018

(65) Prior Publication Data

US 2019/0376056 A1 Dec. 12, 2019

Related U.S. Application Data

(60) Division of application No. 15/245,818, filed on Aug. 24, 2016, now abandoned, which is a continuation-in-part of application No. PCT/KR2016/006728, filed on Jun. 23, 2016.

(30) Foreign Application Priority Data

Jun. 23, 2015 (KR) .......................... 10-2015-0089267

(51) Int. Cl.
| | |
|---|---|
| *C12N 15/10* | (2006.01) |
| *C08L 101/12* | (2006.01) |
| *C08G 73/02* | (2006.01) |
| *C08G 73/06* | (2006.01) |
| *C12Q 1/6886* | (2018.01) |

(52) U.S. Cl.
CPC ........ *C12N 15/1006* (2013.01); *C08L 101/12* (2013.01); *C08G 73/0266* (2013.01); *C08G 73/0611* (2013.01); *C12Q 1/6886* (2013.01); *C12Q 2600/118* (2013.01); *C12Q 2600/156* (2013.01)

(58) Field of Classification Search
CPC ............ C12Q 1/6806; C12Q 2565/607; C12Q 1/6825; C12Q 2563/116; C12Q 2563/157; C12Q 1/6886; C08G 73/0266; C08G 73/0611; C08L 101/12; C12N 15/1006; B01L 2300/0645; C07H 21/04; G01N 27/3335; G01N 27/4146; G01N 33/49; G01N 27/327; G01N 33/5438; G01N 27/126; B03C 5/005; B03C 5/026
See application file for complete search history.

(56) References Cited

U.S. PATENT DOCUMENTS

| | | | | |
|---|---|---|---|---|
| 5,440,025 A * | 8/1995 | Marx | .................... | C12N 15/101 536/25.4 |
| 5,776,672 A * | 7/1998 | Hashimoto | ............ | B01L 7/525 435/5 |
| 2005/0147747 A1 | 7/2005 | Yadav | | |
| 2006/0207878 A1* | 9/2006 | Myung | ............... | G01N 33/5436 204/403.09 |
| 2007/0037153 A1* | 2/2007 | Mandrand | ............ | C12Q 1/6837 435/6.12 |
| 2007/0073049 A1* | 3/2007 | Lee | ......................... | C07H 21/04 536/25.4 |
| 2007/0114128 A1* | 5/2007 | Lau | .................... | G01N 27/3335 204/284 |
| 2009/0124025 A1 | 5/2009 | Hamilton et al. | | |
| 2009/0166205 A1* | 7/2009 | Sundberg | ........... | C12N 15/1006 204/554 |
| 2009/0294303 A1 | 12/2009 | Fischer et al. | | |
| 2010/0041048 A1 | 2/2010 | Diehl et al. | | |
| 2010/0330706 A1 | 12/2010 | Wei et al. | | |
| 2014/0315195 A1* | 10/2014 | Wong | .................... | C12Q 1/6806 435/6.11 |
| 2015/0027891 A1* | 1/2015 | Puleo | ..................... | B01D 57/02 204/543 |
| 2015/0147747 A1 | 5/2015 | Cho | | |
| 2015/0283553 A1* | 10/2015 | Charlot | .................. | B03C 5/026 204/547 |

FOREIGN PATENT DOCUMENTS

| | | |
|---|---|---|
| JP | 2011-529691 A | 12/2011 |
| KR | 10-2007-0041952 A | 4/2007 |
| KR | 10-2009-0037670 A | 4/2009 |
| KR | 10-2014-0088646 A | 7/2014 |
| KR | 10-2015-0059992 A | 6/2015 |
| WO | 2008/047364 A2 | 4/2008 |

OTHER PUBLICATIONS

Sonnenberg et al "Rapid electrokinetic isolation of cancer-related circulating cell-free DNA directly from blood" Clincal Chemistry Mar. 1, 2014 60:3, pp. 500-509. (Year: 2014).*
Lee et al, (Post Art) A novel strategy for highly efficient isolation and analysis of circulating tumor-specific cell-free DNA from lung cancer patients using a reusable conducting polymer nanostructure, 2016, Biomaterials, 101, 251-257. (Year: 2016).*
The extended European Search Report for corresponding EP Application No. 16814724.7, dated Nov. 22, 2018.
Sonnenberg et al., "Dielectrophoretic isolation and detection of cancer-related circulating cell-free DNA biomarkers from blood and plasma", Electrophoresis, vol. 35, pp. 1828-1836, (2014).
Velusamy et al., Comparison Between DNA Immobilization Techniques on a Redox Polymer Matrix, American Journal of Analytical Chemistry, vol. 2, pp. 392-400, (2011).

(Continued)

*Primary Examiner* — Narayan K Bhat
(74) *Attorney, Agent, or Firm* — Vorys, Sater, Seymour & Pease LLP; Mih Suhn Koh

(57) ABSTRACT

Disclosed is a structure for detecting cell-free DNA using a conductive polymer and the use thereof. More particularly, a nanostructure composed of a surface-modified conductive polymer for isolating and detecting cell-free DNA is disclosed. By using the nanostructure, cell-free DNA including circulating tumor DNA, can be effectively detected and isolated.

7 Claims, 30 Drawing Sheets

Specification includes a Sequence Listing.

(56) References Cited

OTHER PUBLICATIONS

Zhu et al., "Electrochemically fabricated polyaniline nanowire-modified electrode for voltammetric detection of DNA hybridization", Electrochimica Acta, 51: 3758-3762, (2006).

Fehm et al., "Cytogenetic Evidence That Circulating Epithelial Cells in Patients with Carcinoma Are Malignant", Clinical Cancer Research, vol. 8, pp. 2073-2084, (2002).

Jeon et al., "Efficient Capture and Isolation of Tumor-Related Circulating Cell-Free DNA from Cancer Patients Using Electroactive Conducting Polymer Nanowire Platforms", Theranostics, vol. 6, Issue 6, pp. 828-836, (2016).

Lee et al., "A novel strategy for highly efficient isolation and analysis of circulating tumor-specific cell-free DNA from lung cancer patients using a reusable conducting polymer nanostructure", Biomaterials, vol. 101, pp. 251-257, (2016).

Nagrath et al., "Isolation of rare circulating tumour cells in cancer patients by microchip technology", Nature, vol. 450, pp. 1235-1239, with two pages for methods, (2007).

Jeon et al., "High-Purity Isolation and Recovery of Circulating Tumor Cells using Conducting Polymer-deposited Microfluidic Device", Theranostics, vol. 4, No. 11, pp. 1123-1132, (2014).

Stratagene catalogue, 1988, p. 39.

The Notice of Rejection in corresponding JP Application No. 2017-566695, dated Jan. 10, 2019.

Velusamy et al., "Comparison Between DNA Immobilization Techniques on a Redox Polymer Matrix", American Journal of Analytical Chemistry, 2011, vol. 2, pp. 392-400.

Zhu et al., "Electrochemically fabricated polyaniline nanowire-modified electrode for voltammetric detection of DNA hybridization", Electrochimica Acta, 2006, vol. 51, pp. 3758-3762.

Office Action dated Aug. 3, 2021, in corresponding CN Application No. 201680047982.7, 9 pages.

Lim et al., "DNA Binding to Conducting Polymer Films", Mat. Res. Soc. Symp. Proc., 1992, vol. 255, No. 1, pp. 195-200.

* cited by examiner 0.8 V 1.8 V

SEQUENCE LISTING

```
<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: K-RAS forward primer

<400> SEQUENCE: 1
actgaatata aacttgtggt agttggacct                                    30

<210> SEQ ID NO 2
<211> LENGTH: 30
<212> TYPE: DNA
<213> ORGANISM: Artificial Sequence
<220> FEATURE:
```

```
<223> OTHER INFORMATION: K-RAS reverse primer

<400> SEQUENCE: 2
actcatgaaa atggtcagag aaacctttat                              30

<210> SEQ ID NO 3
<211> LENGTH: 24
<212> TYPE: DNA
<213> ORGANISM: Artificial Sequence
<220> FEATURE:
<223> OTHER INFORMATION: EGFG (Exon 19) forward primer

<400> SEQUENCE: 3
gcaccatctc acaattgcca gtta                                    24

<210> SEQ ID NO 4
<211> LENGTH: 21
<212> TYPE: DNA
<213> ORGANISM: Artificial Sequence
<220> FEATURE:
<223> OTHER INFORMATION: EGFG (Exon 19) reverse primer

<400> SEQUENCE: 4
aaaaggtggg cctgaggttc a                                       21

<210> SEQ ID NO 5
<211> LENGTH: 19
<212> TYPE: DNA
<213> ORGANISM: Artificial Sequence
<220> FEATURE:
<223> OTHER INFORMATION: P53 forward primer

<400> SEQUENCE: 5
cagcacatga cggaggttg                                          19

<210> SEQ ID NO 6
<211> LENGTH: 21
<212> TYPE: DNA
<213> ORGANISM: Artificial Sequence
<220> FEATURE:
<223> OTHER INFORMATION: P53 reverse primer

<400> SEQUENCE: 6
tcatccaaat actccacacg c                                       21

<210> SEQ ID NO 7
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 7
ggagcgagat ccctccaaaa t                                       21

<210> SEQ ID NO 8
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 8
ggctgttgtc atacttctca                                         20
```

```
<210> SEQ ID NO 9
<211> LENGTH: 23
<212> TYPE: DNA
<213> ORGANISM: Artificial Sequence
<220> FEATURE:
<223> OTHER INFORMATION: EGFR L858R forward primer

<400> SEQUENCE: 9
gcagcatgtc aagatcacag att                                                  23

<210> SEQ ID NO 10
<211> LENGTH: 25
<212> TYPE: DNA
<213> ORGANISM: Artificial Sequence
<220> FEATURE:
<223> OTHER INFORMATION: EGFR L858R reverse primer

<400> SEQUENCE: 10
cctccttctg catggtattc tttct                                                25

<210> SEQ ID NO 11
<211> LENGTH: 16
<212> TYPE: DNA
<213> ORGANISM: Artificial Sequence
<220> FEATURE:
<223> OTHER INFORMATION: Probe

<400> SEQUENCE: 11
agtttggcca gcccaa                                                          16
```

NANOSTRUCTURE FOR DETECTING CELL-FREE DNA USING CONDUCTIVE POLYMER AND THE USE THEREOF

CROSS-REFERENCE TO RELATED APPLICATION

This application claims priority to and the benefit of Korean Patent Application No. 2015-0089267, filed on Jun. 23, 2015 and International Patent Application No. PCT/KR2016/006728, filed on Jun. 23, 2016, the disclosure of which is incorporated herein by reference in its entirety.

The present invention was undertaken with the support of No. 1510070 and No. 1611170 grant funded by a National Cancer Center, from the Ministry of Health and Welfare, the Republic of Korea.

SEQUENCE LISTING

The Sequence Listing submitted in text format (.txt) filed on Aug. 21, 2019, named "SequenceListing.txt", created on Aug. 21, 2019 (2.14 KB), is incorporated herein by reference.

BACKGROUND

1. Field of the Invention

The present invention relates to a structure for detecting cell-free DNA using a conductive polymer and the use thereof, and more particularly, to a nanostructure composed of a surface-modified conductive polymer for isolating and detecting cell-free DNA, such as circulating tumor DNA.

2. Discussion of Related Art

The existence of circulating cell-free DNA was first reported by Mandel and Metais in 1948. Circulating cell-free DNA (cfDNA) has been studied in a variety of physiological and pathological conditions such as inflammatory disorders, oxidative stress and malignancy. In healthy subjects, a blood concentration of cfDNA is 0-100 ng/ml and an average blood concentration thereof is 30 ng/ml. Assuming that a DNA content in a normal cell is 6.6 pg, the value corresponds to 0 to 15,000 genome equivalents on average per ml of blood and an average number of genomes is 5000 per ml. Here, most DNA is double-stranded and is present as a nucleoprotein complex.

Although an accurate mechanism related with the release of free DNA into the blood steam is unclear, it appears to be affected by a combination of apoptosis, necrosis and active release from cells.

Circulating cell-free DNA is a potentially useful biomarker. DNA levels and fragmentation patterns suggest interesting possibilities for diagnostic and prognostic purposes. Recently, Bartoov et al. introduced a method of evaluating fertility of a male subject based on the measurement of cfDNA in a fluid sample from a subject (WO2008/047364). They also suggested a method of treating a subfertile man by administering DNase. Further, cell-free DNA was suggested as a biomarker for non-invasive monitoring of malignant and benign proliferation and inflammatory conditions, e.g., endometriosis.

In particular, a non-invasive test utilizing circulating tumor cells (CTCs) or circulating tumor DNA (ctDNA) among circulating cell-free DNA, which is extracted and isolated from blood, in diagnosing and monitoring cancer according to a method of detecting cancer-specific genes is anticipated to contribute to the field of cancer diagnosis.

A cancer diagnostic method using a non-invasive blood sample is a very interesting method and currently attracts great attention. If CTCs and ctDNA can be effectively isolated or captured from a blood sample, they can form the foundation of diagnostic and therapeutic strategies. In addition, since a therapeutic method targeting genetic changes of tumors due to resistance to anticancer drugs can be periodically selected, the effects of a conventional cancer treatment can be maximized.

Circulating tumor cells (CTCs), as epithelial cells present in the blood of a patient with various malignant solid tumors, are derived from a primary tumor clone and are malignant (Fehm et al. [Clin. Cancer Res. 8: 2073-84, 2002]). In addition, it was reported that CTCs can be considered as diagnosis independent in developing carcinomas.

The detection and calculation of circulating tumor cells are important in managing patients for several reasons. Circulating tumor cells may be detected before primary tumor formation, thus allowing early stage diagnosis. Since the circulating tumor cells respond to a treatment and decrease in number, the calculation of CTCs allows monitoring of the effects of a given therapeutic regimen. Such circulating tumor cells can be used as a tool for monitoring disease recurrence in a patient who is administered with an adjuvant and having an unpredictable disease.

In blood, there are very few CTCs and ctDNA. For example, there is approximately one CTC and ctDNA per $10^8$ to $10^9$ blood cells. Accordingly, several CTC isolation methods have been proposed. For example, a method of using a microfluidic device wherein a capture antibody is bound to magnetic particles, to which anti-EpCAM (epithelial cell adhesion molecule) antibody is immobilized, or to the resin surfaces with columnar structures, etc., a method of isolating by means of a filter utilizing the difference in sizes of CTCs and blood cells, and the like are known isolation methods (Isolation of rare periphery circulating tumor cells in cancer patients by microchip technology. Sunitha Nagrath et al. Nature, 2007, 450: 1235-1239).

To extract ctDNA, a commercially available kit is generally used. In the Qiagen Circulating Nucleic Acid Kit, DNA attachment is induced using a positively charged silica membrane, and the attached DNA is isolated by changing pH. However, using this kit, collection efficiency is still low.

Laurent group in France introduced a technology of quantifying a KRAS tumor formation gene by identifying ctDNA present in the blood plasma of a rectal cancer patient using droplet-based digital PCR. Diamond group in Pennsylvania University, US, conducted research into attaching negatively charged DNA using positively charged polyethylenimine nanoparticles. Particularly, this technology allows effective isolation by connecting a photocleavable ligand to surfaces of nanoparticles and then irradiating DNA captured by the ligand with light. In Wang group at Dezhou University, China, a positively charged polymer was attached to magnetic nanoparticles, and then effective attachment and isolation of genomic DNA was achieved through changing pH.

However, current methods of detecting ctDNA have many problems. First, there are problems such as long detection time, complex processing, high cost, and low collection efficiency. In particular, since ctDNA is detected in advanced cancer patients rather than early cancer patients, there is an urgent need for ultrasensitive detection/isolation technology.

Accordingly, the present inventors confirmed that the adhesion of a nanostructure of ctDNA is greatly increased by positively charging a surface of the nanostructure, which is prepared using a conductive polymer, and the ctDNA is effectively released from the nanostructure by an electric signal and completed the present invention.

SUMMARY OF THE INVENTION

Therefore, the present invention has been made in view of the above problems, and it is a main objective of the present invention to provide a structure for detecting and/or isolating cell-free DNA (cfDNA) using a conductive polymer and a kit including the same.

It is another objective of the present invention to provide a method of detecting and/or isolating cfDNA using the conductive polymer.

It is still another objective of the present invention to provide information for diagnosing the onset of and a prognosis for cancer based on a result of the detection and isolation of cfDNA.

It is yet another objective of the present invention to provide a method of diagnosing the onset of and a prognosis for cancer based on a result of the detection and isolation of cfDNA.

In accordance with the present invention, the above and other objectives can be accomplished by a provision of a structure for detecting and isolating cell-free DNA, preferably circulating tumor DNA (ctDNA), including a surface-modified conductive polymer.

Here, since the cell-free DNA has a negative charge, the surface-modified conductive polymer has preferably a positive charge.

The nanostructure may have a shape of, without being limited to, a nanochip, a nanodot, a nanorod, or a nanowire.

The conductive polymer may be selected from the group consisting of polyacetylene, polyaniline, polypyrrole, polythiophene, and poly sulfur nitrides. Most preferably, the conductive polymer is polypyrrole.

In accordance with another aspect of the present invention, there is provided a kit for detecting and isolating cell-free DNA, wherein the kit includes the structure.

In accordance with still another aspect of the present invention, there is provided a method of detecting and isolating cell-free DNA, the method including:

(i) positively charging a surface of a conductive polymer forming a nanostructure;

(ii) treating the conductive polymer with a biological substance to attach the cfDNA to the conductive polymer; and (iii) detecting the cfDNA with the conductive polymer or releasing the cfDNA from the conductive polymer by applying an electric signal.

Here, the biological substance may be blood, bone marrow, pleural fluid, peritoneal fluid, spinal fluid, urine, or saliva and preferably blood.

In step (ii), the cfDNA is preferably attached by applying an electric signal at 0.8 to 1.2 V for 20 to 40 seconds.

In step (iii), the cfDNA is preferably detected or isolated by applying an electric signal at −1.3 to −1.0 V for 4 to 6 minutes.

Depending on the used conductive polymer type and the DNA type to be detected, the magnitude of an electric signal may be suitably controlled by those skilled in the art.

In accordance with still another aspect of the present invention, there is provided a method of providing information to diagnose the onset of and a prognosis for cancer in a subject, the method comprising detecting and/or isolating circulating tumor DNA (ctDNA) from a sample using the structure, and analyzing the detected or isolated ctDNA.

In accordance with still another aspect of the present invention, there is provided a method of diagnosing the onset of and a prognosis for cancer in a subject, the method including detecting/isolating circulating tumor DNA (ctDNA) from a sample using the structure for detecting and isolating cell-free DNA and analyzing the detected or isolated ctDNA.

Here, the cancer may be selected from the group consisting of carcinoma, lymphoma, blastoma, sarcoma, liposarcoma, neuroendocrine tumor, mesothelioma, schwannoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, brain cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney and renal cancer, prostate cancer, vulval cancer, thyroid cancer, hepatic carcinoma, anal carcinoma, penile carcinoma, testicular cancer, esophageal cancer, biliary tract, and head and neck cancer. Preferably, the cancer is breast cancer, lung cancer, gastric or stomach cancer, liver cancer, or pancreatic cancer.

The analyzing according to the present invention may include the analysis of the concentration, copy number, or sequences of ctDNA in a sample. Here, information that cancer is developed or advanced when the amount (concentration) or copy number of the ctDNA increases may be provided As described above, the nanostructure composed of the surface-modified conductive polymer according to the present invention may be used in various applications involving detection or isolation of circulating cell-free DNA (cfDNA).

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
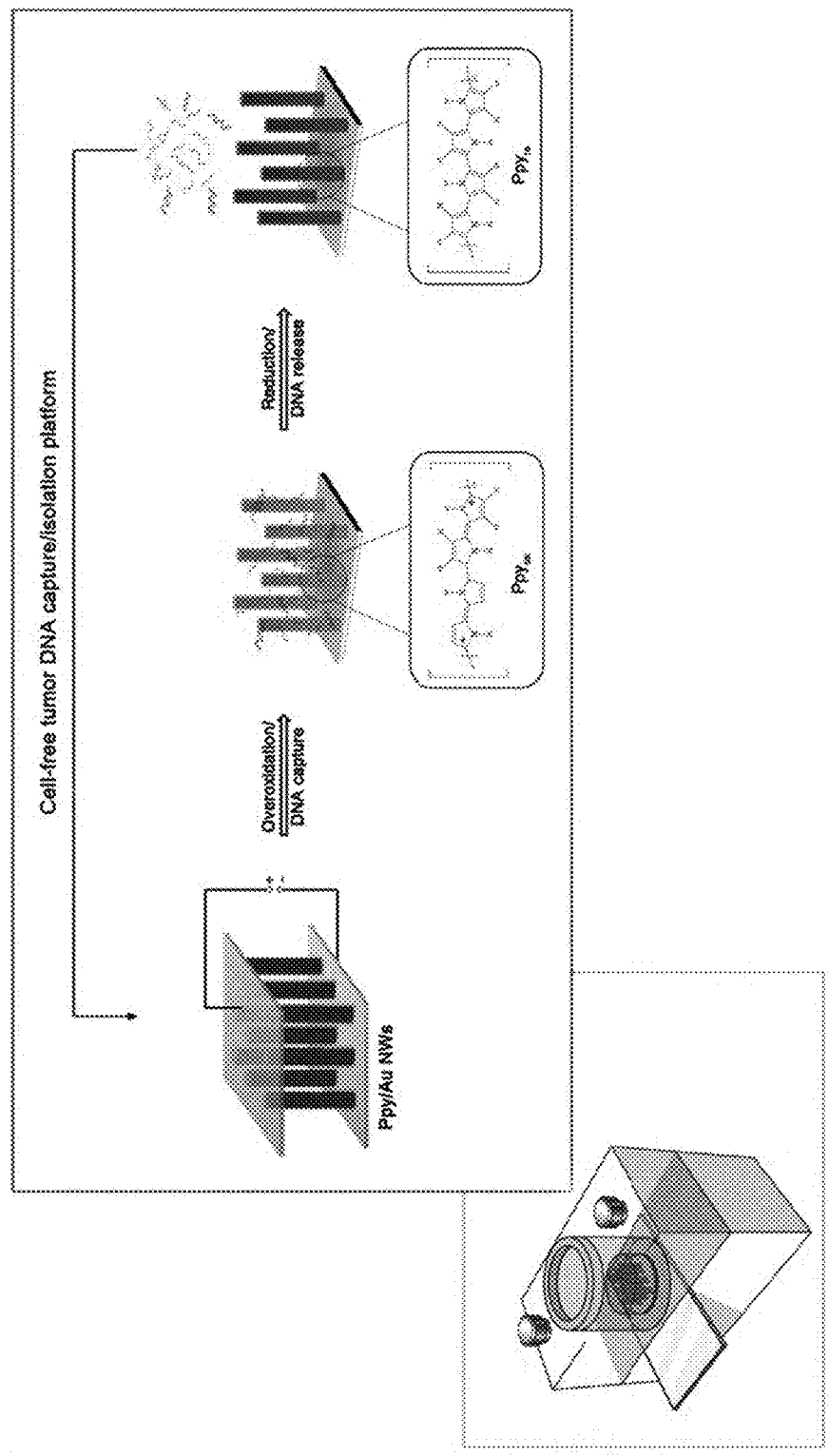
FIG. 1 schematically illustrates a method of detecting and isolating circulating cell-free DNA (cfDNA) using the nanostructure, Ppy/Au NWs, of the present invention.
Figure 2:
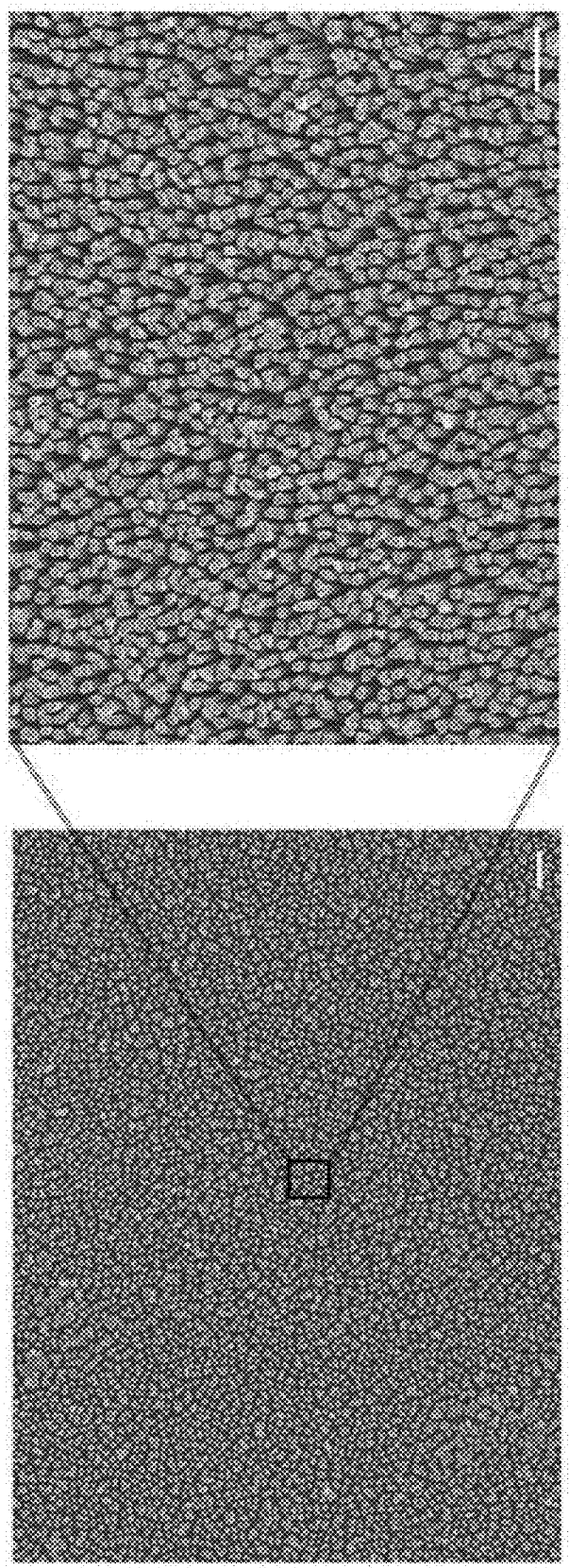
FIG. 2 illustrates a FE-SEM image of a top view of the nanostructure, Ppy/Au NWs, of the present invention.

Terms used in the present invention are defined below.

The term "subject" or "patient" refers to any single subject, that includes human, bovine, canine, guinea pig, rabbit, chicken, insects, etc., requiring therapy. In addition, the subject includes any subject that does not exhibit clinical features related to a certain disease and participates in clinical test research or epidemiological research or a subject used as a control. In an embodiment of the present invention, the subject is human.

The term "circulating tumor cells" (CTCs) refer to any cancer cells detected in a sample of a subject. CTCs are commonly epithelial cells exfoliated from solid tumor which is detected at a very low concentration in circulating blood of an advanced cancer patient. CTCs also can be derived from primary, secondary, or tertiary tumor. The "circulating tumor cells" (CTCs) include non-tumor cells that are not commonly detected in circulating blood, for example, circulating epithelial or endothelial cells, as well as cancer cells. Accordingly, tumor cells and non-tumor epithelial cells are also included within the scope of CTCs of the present invention.

The term "cancer" includes various cancer types known in the art including, without being limited to, dysplasias, hyperplasias, solid tumors and hematopoietic cancers. Many cancer types are known to metastasize and spread circulating tumor cells and are metastatic, like, for example, secondary cancer derived from metastasized primary cancer. Examples of additional cancers may include, without being limited to, cancers of the following organs or systems: brain, cardiac, lung, gastrointestinal, genitourinary tract, liver, bone, nervous system, gynecological, hematologic, skin, breast, and adrenal glands. Examples of additional types of cancer cells include, without being limited to, gliomas (Schwannoma, glioblastoma, astrocytoma), neuroblastoma, pheochromocytoma, paraganlioma, meningioma, adrenalcortical carcinoma, medulloblastoma, rhabdomyosarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

The term "sample" refers to any sample suitable for methods according to the present invention. Supply sources of samples include whole blood, bone marrow, pleural fluid, peritoneal fluid, central spinal fluid, urine, saliva, and bronchial washes. In an aspect, the sample is a blood sample including, for example, whole blood or any fraction or component thereof. A blood sample suitable for use in the present invention may be extracted from any sources that includes blood cells or components thereof, for example, veinous blood, arterial blood, peripheral blood, tissue, cord blood, and the like.

The term "protein" includes proteinous fragments, analogous, and derivatives having biological activities or functions identical to those of a native protein.

The term "polynucleotide" or "nucleic acid" refers to a polymeric form of nucleotides of any length, such as deoxyribonucleotides as well as ribonucleotides. The term only refers to a primary structure of a molecule, i.e., single- or double-strand DNA or RNA. It also includes known modification types, for example, labels which are known in the art, methylation, "caps", substitution of one or more of the naturally occurring nucleotides with an analog, internucleotide modifications, such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified polynucleotide forms.

The term "primer" refers to an oligonucleotide sequence which is hybridized to a complementary RNA or DNA target polynucleotide and is capable of acting as a point of initiation of synthesis for stepwise synthesis to polynucleotide from mononucleotide through, for example, nucleotidyl-transferase action that occurs due to a polymerase chain reaction.

The term "functional equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. A substantially equivalent, e.g., mutant or amino acid sequences, according to the invention preferably have at least 80% sequence identity with a listed amino acid sequence, more preferably at least 90% sequence identity. Substantially equivalent nucleotide sequences of the invention can have lower percent sequence identities, for example, when the redundancy or degeneracy of the genetic code is considered. Preferably, a nucleotide sequence has at least about 65% identity, more preferably at least about 75% identity, most preferably at least about 95% identity.

Anticancer drug "tolerance" means that genes of cancer cells are changed in response to an anticancer drug, and thus the cancer cells avoid the attack of the anticancer drug to reduce the effect of an anti-cancer treatment. The term "tolerance" can be used in the same meaning as the term "resistance."

"Treatment" is an approach for obtaining beneficial or desired clinical results. "Treatment" or "alleviation" of a disease, a disorder or a condition means that the severity of the condition, disorder or disease and/or undesired clinical symptoms is reduced and/or the progression of the condition, a disorder or disease is delayed or prolonged, compared to the case in which the condition, disorder or disease is not treated. For example, in the treatment of obesity, a reduction in body weight, for example, a weight loss of at least 5%, is a desired result. Beneficial or desired results to accomplish the purposes of the present invention can include, without being limited to, relief or amelioration of one or more symptoms, diminishing the extent of disease, stabilized (i.e. not worsened) state of disease, delaying or slowing disease progression, amelioration or alleviation of a disease state, and remission (partial or total), whether detectable or undetectable. "Treatment" can also mean prolonged survival, compared to expected survival when treatment is not conducted. In addition, "treatment" is not necessarily accomplished by administration of a single dose and is often accomplished by administration of a series of doses. Accordingly, a therapeutically effective amount, an amount sufficient to alleviate, or an amount sufficient to treat a disease, disorder or condition can be administered once or more.

The term "about" refers to a quantity, level, value, number, frequency, percentage, dimension, size, amount, weight, or length that varies by 30, 25, 20, 25, 10, 9, 8, 7, 6, 5, 4, 3, 2 or 1% relative to a reference quantity, level, value, number, frequency, percentage, dimension, size, amount, weight, or length.

Throughout the present specification, it is to be understood that the terms such as "comprise" and/or "comprising" are intended to indicate the existence of steps or elements or a group of steps or elements and are not intended to preclude the possibility that one or more other steps or elements or groups thereof may exist or may be added, unless otherwise mentioned.

Hereinafter, the present invention will be described in detail.

The present invention relates to a structure for detecting and isolating cell-free DNA using a conductive polymer and the use thereof.

In particular, the present invention relates to a nanostructure composed of a surface-modified conductive polymer to effectively detect and isolate cell-free DNA including circulating tumor DNA and the use thereof.

<Conductive Polymer>

The structure for detecting cell-free DNA according to the present invention is composed of a conductive polymer.

Since conductive polymers have electrical, magnetic, optical properties of a metal or semiconductor with ductility of a polymer and easy manufacturability, they are broadly used as useful materials in various industrial fields, as well as chemistry and physics. In particular, the conductive polymers have various advantages, such as easy processability, high electrical conductivity, superior body compatibility, environmental stability, and reversible volumetric change and thus are used in biosensors, tissue engineering, neural probes, drug delivery, bio-operators.

Examples of a conductive polymer that may be used in the present invention include, without being limited to, polypyrrole, polyacetylene, polyaniline, polythiophene, poly sulfur nitride, and derivatives thereof.

Examples of a preferred conductive polymer include polypyrrole. Polypyrrole has superior stability in vivo and the repetitive expansion due to oxidation and contraction due to reduction and thus is selected as a material of medical operators and micropumps for body transplantation. In particular, a conductive polymer exhibits a reversible volumetric expansion and contraction phenomenon due to a doping/de-doping mechanism with anions in an electropolymerization process, thus attracting attention as a drug delivery material. In addition, polypyrrole may be coated on a conductive film due to oxidation-reduction reaction according to electropolymerization and is used for practical purposes in manufacturing chemical sensors, biosensors, supercapacitors, etc.

Polypyrrole may be synthesized according to the following method, or commercially available polymers may be used.

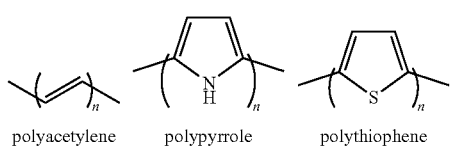

polyacetylene   polypyrrole   polythiophene

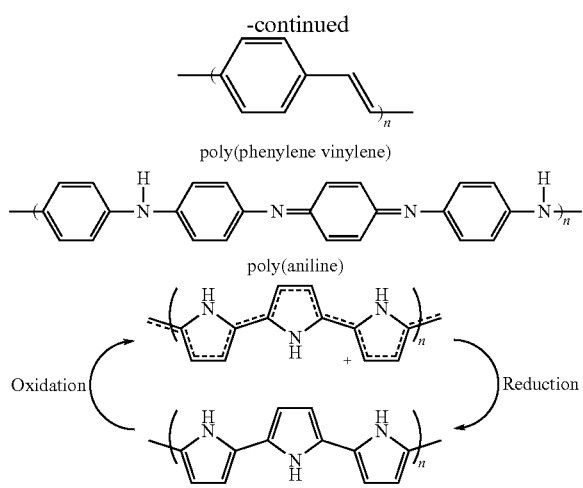

poly(phenylene vinylene)

poly(aniline)

In particular, when polypyrrole is used, the charge of a polypyrrole nanostructure is changed only by electrical stimulation, and thus, a conventional pretreatment process according to DNA isolation is not required. In addition, DNA attached to a surface of polypyrrole can also be easily collected by electrical stimulation without a separate process.

Hereinafter, the compounds include the compounds itself, pharmaceutically acceptable salts, hydrates, solvates, isomers, and pro-drugs thereof, unless otherwise mentioned.

The conductive polymer compound may be prepared according to methods known in the art, methods modified therefrom, etc., and commercial compounds may also be taken and used. That is, various methods based on technology in the art may be suitably modified and used referring to generally known methods. For example, modification obvious to those skilled in the art, for example, suitably protecting an interfering group, substituting with another reagent generally known in the art, or changing a reaction condition according to general manners, may be successfully performed.

<Structure Formed of Conductive Polymer>

In an aspect, the present invention relates to a conductive polymer for cfDNA detection or isolation, preferably a structure for ctDNA detection or isolation, and the use thereof.

Figure 3:
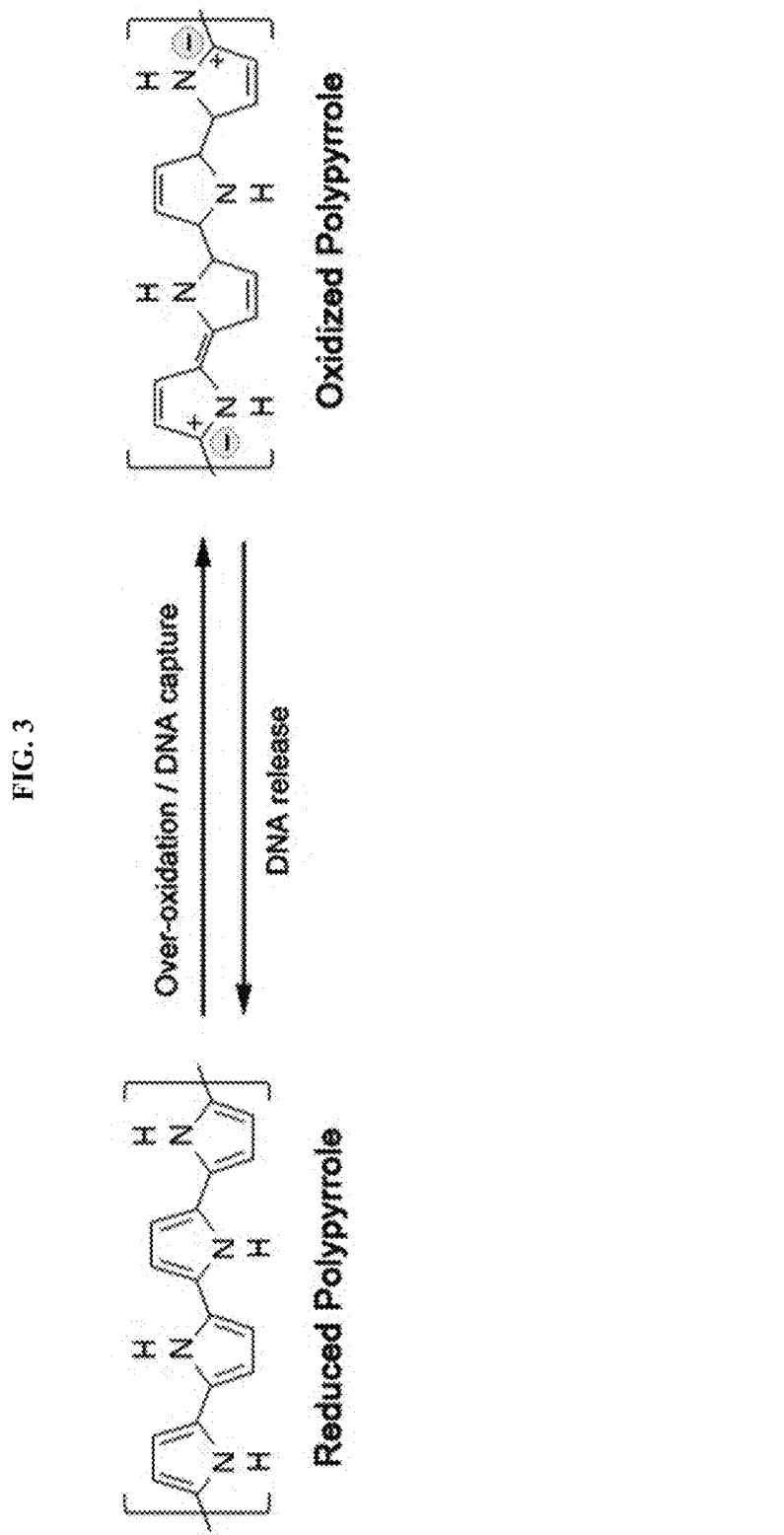
FIG. 3 illustrates a DNA capture and release mechanism according to the oxidation-reduction of a conductive polymer polypyrrole.

In particular, as illustrated in FIG. 3, the conductive polymer constituting the structure is electrochemically surface-modified, thus increasing the adhesion property and specificity of circulating cell-free DNA.

Electrochemical Surface Modification

The technology of fixing a biomaterial to an electrodeposited conductive polymer is required to recognize an analyte.

In the present invention, a method of electrochemically activating a surface of a polymer to fix a biomaterial to the polymer, among various fixation technologies, is used. By this method, a desired material is positively or negatively charged to be selectively fixed to a desired site.

Preferably, a surface of the conductive polymer is modified by electrical stimulation and thus has positive charge to facilitate isolation of DNA having negative charge.

A substance having positive charge which may be used to change surface characteristics of the nanostructure composed of a conductive polymer is preferably one or more selected from the group consisting of amino silane including aminopropyltriethoxysilane (APTES), nylon, nitrocellulose, spermidine, and polylysine. Since the characteristics of a surface having positive charge of the nanostructure depend on a positively charged material type and a treatment concentration thereof, the size of DNA may be determined according to the surface characteristics of the nanostructure, which are controlled by the material type treated on the surface of the nanostructure or a treatment concentration with the material.

It is obvious that surface modification of the conductive polymer is suitably performed by those skilled in the art before or after the formation of the structure or upon formation of the structure.

The structure for cfDNA detection or isolation composed of the surface-modified conductive polymer may be a flat structure or a nanostructure.

In an embodiment of the present invention, a nanostructure is used to modify the conductive polymer to be similar to an in vivo environment.

In a non-restrictive example, a three-dimensional biomimic structure, such as a nanoporous structure or a nanowire structure, may be used. Such a nanostructure is similar to an extracellular matrix in vivo, thus improving the growth and differentiation of cells in vivo and maximizing interaction with living tissue.

The nanostructure may be manufactured according to a generally known method. For example, a hybrid method, such as (i) a vapor-phase particle growth method including laser pyrolysis used in nanoparticles synthesis or atomic layer deposition used in thin film deposition, (ii) a liquid-phase growth method including a colloidal method for nanoparticle formation and mono-layer magnetic coupling technologies, (iii) a solid-phase particle preparation method, such as a phase separation method, to prepare metal nanoparticles, (iv) a vapor-liquid-solid (VLS) nanowire growth method, etc. may be used.

In the present invention, a nanorod or a nanowire, which is electrically manufactured in a mold and grows in a solution or anisotropically grows, may be used. The shape of the nanostructure that may be formed of a conductive polymer is not specifically limited, but the nanostructure is most preferably manufactured as a nanowire structure.

The nanowire refers to a structure having a nanometer-scale diameter and a several hundred nanometer to micrometer-scale length.

The size and interfacial and electrical characteristics of the nanowire may be accurately controlled in a synthesis process thereof. A large number of such synthesized nanowires may be advantageously assembled in parallel.

Recently, mold polymerization is broadly used in manufacturing a functional nanomaterial. The length, diameter, and density of a polymerized nanostructure may be controlled by varying a mold type and a deposition condition.

Preferably, anodic aluminium oxide (AAO) having nanopores produced by anodization may be used as a template. The porous AAO is mainly used as a general template for producing nanowires or nanotubes made of metal or ceramic. The AAO is thermally stable and, at high density ($10^9$ to $10^{11}/cm^2$), has vertically arranged nanochannels. In an embodiment of the present invention, Au nanowires with nanopores were produced using the AAO produced by anodization.

In the free-standing nanowire structure of the present invention, a surface of each of nanowire columns is modified, and thus, the adhesion to ctDNA greatly increases, and, in addition, due to a wide surface area by various lengths and diameters, the nanowire structure of the present invention has greatly increased detection effect.

In another embodiment, a nanochip or nanodot structure may be simply manufactured using the conductive polymer of the present invention.

It was confirmed through an example of the present invention that the aforementioned nanostructure can be simply manufactured into a nanochip or a nanodot structure, as well as the nanowire, by electrochemically modifying a surface of the polypyrrole polymer upon coating of the polymer, and thus, the adhesion to ctDNA greatly increases and ctDNA detection efficiency can be increased through voltage control.

As such, the structure composed of the conductive polymer of the present invention responds only to external electrical stimulation, and thus, attached ctDNA can be isolated only by an electric signal. Accordingly, ctDNA may be specifically and effectively detected.

<cfDNA>

The structure composed of the conductive polymer of the present invention is useful for detecting and isolating circulating cell-free DNA (cfDNA), particularly circulating tumor DNA (ctDNA).

Circulating cell-free DNA is a generic term for all DNA types released from cells present in blood. Regardless of the origins and sources of DNA, all DNA types may be a subject to be detected or isolated according to the present invention. However, most preferably, the circulating cell-free DNA may be circulating tumor DNA (ctDNA) released from circulating tumor cells (CTCs).

Blood from a cancer patient includes tumor DNA fragments, i.e., ctDNA, released into blood by the death of cancer cells due to apoptosis and necrosis. In general, contents from normal cells in blood are instantly treated by macrophagocytes, but the amount of ctDNA released from destroyed cancer cells is larger than the amount which can be treated by phagocytes. It was reported that, in the case of a cancer patient having 100 g of tumor, i.e., $3 \times 10^{10}$ cancer cells, up to 3.3% of cfDNA was released into blood every day. On average, ctDNA exists as small fragments having 70 to 200 base pairs to large fragments having 21 kilo base pairs. However, most cancer-derived cfDNA exists as small fragments of 200 bp or less.

In general, a normal person has DNA at an average amount of less than 30 ng/ml in blood, while cancer patients have ctDNA at an average amount of 180 ng/ml in blood. In the case of primary cancer patients, the amount of ctDNA present in blood is reduced to about half of that of a normal person upon removal of tumor parts. On the other hand, in the cases of metastatic cancer patients, still high ctDNA values are exhibited.

Therefore, ctDNA plays a very important role regarding the detection of initial cancer as well as monitoring of therapeutic processes. That is, when ctDNA present in blood is detected, the detected ctDNA can become an important clue for understanding the status of tumor.

In particular, since ctDNA has a half-life of less than two hours, it can provide the latest information about tumor, i.e., cancer cell-specific mutation and other genetic changes, which is very useful.

Conventional protein markers are disadvantageous in that a protein concentration increase in blood may be caused by, other than cancer development, normal cells, and thus, false-positive detection may be exhibited. In addition, since most protein markers are present in blood over several weeks, they have limitation in giving accurate information about a current status of a tumor. On the other hand, cfDNA of the present invention, which is a subject for detection or isolation, preferably ctDNA, can address such issues.

Meanwhile, examples of a sample source of the present invention used to detect or isolate ctDNA include whole blood, bone marrow, pleural fluid, peritoneal fluid, central spinal fluid, urine, saliva, and bronchial wash. In a preferred embodiment, the sample is a blood sample including, for example, whole blood or any fraction or component thereof.

Examples of a blood sample suitable for use in the present invention include blood cells or components thereof. For example, the blood sample may be extracted from any source including vein, artery, peripheral blood, tissue, cord blood, etc. For example, the sample may be obtained and treated according to generally known general clinical methods (for example, procedures to collect and treat whole blood). In an aspect, the sample may be, for example, peripheral blood collected from a subject having cancer.

The amount (volume) of the sample may be suitably selected and determined by those skilled in the art. A general amount of the sample is 1 to 20 ml, preferably 3 to 7 ml.

In general, body fluid (particularly, blood) used as a sample may be diluted, for example, 2 to 20 fold with phosphate buffered saline (PBS) (0.251 mM EDTA-containing PBS according to purpose), followed by filtration. In particular, when a blood amount or blood cell number is large, pretreatment may be carried out.

<Capture Method>

In another aspect, the present invention relates to a method of detecting and isolating circulating cell-free DNA (cfDNA) using the nanostructure. A conceptual schematic diagram of this method is illustrated in FIG. 1.

In an embodiment, the method may include the following processes:

(i) a step of positively charging a surface of a conductive polymer forming a nanostructure;

(ii) a step of treating the conductive polymer with a biological substance to attaching the (cfDNA) to the conductive polymer; and (iii) a step of detecting the cfDNA with the conductive polymer or releasing the cfDNA from the conductive polymer by applying an electric signal.

As described above, a flat structure is formed, or a nanostructure, e.g., a nanowire structure or a nanochip structure, is formed using a conductive polymer having various diameters and lengths. Subsequently, surfaces of conductive polymers are modified by an electrochemical method.

Here, the electrochemical method may be any generally known method. A surface of the conductive polymer may be modified depending on charge characteristics of DNA to be detected or isolated. In a preferred embodiment, the surface of conductive polymer is positively charged to facilitate attachment and isolation of cfDNA having negative charge.

In particular, when a nanostructure is formed of conductive polymers having various diameters and lengths, a surface of the structure becomes rough and thus a ratio of a volumetric area relative to a surface increases. Accordingly, a much larger amount of cfDNA may be attached to the surface of the structure (DNA capture). In addition, such a structure may increase interaction with cfDNA.

Next, a biological substance sample, preferably blood, is treated with such a structure, and thereby cell free DNA (cfDNA) attaches to the conductive polymer.

Here, attachment of cfDNA to the conductive polymer is preferably carried out by applying an electric signal of 0.8 to 1.2 V for 20 to 40 seconds.

In particular, when electropolymerization was performed to increase the surface roughness of the Ppy nanochip structure, various voltages, i.e., 0.8 V to 1.8 V, were used.

The surface roughness increases with increasing voltage upon electropolymerization and thus a surface area greatly increases and DNA-binding sites increase. Accordingly, DNA capture/release efficiency increases. In an actual analysis, a voltage of 1.5 V was added to a mixture solution of 0.1 M pyrrole and 0.01 M PSS for five minutes, and, in this case, the Ppy nanochip structure showed the highest DNA capture efficiency. Accordingly, the condition was used as the basic condition for manufacturing the Ppy nanochip structure. A Ppy nanochip structure was manufactured by electropolymerizing at 1.5 V for five minutes, and then, to maximize the positive charge of a Ppy surface, a voltage of +1.8 V was applied for two minutes in 1 M Tris-HCl buffer to induce the over-oxidation of Ppy. The over-oxidized Ppy nanochip structure was incubated in blood plasma from a patient, and then DNA capture was attempted by applying a voltage of +1.0 V for 30 seconds. As a result, it was confirmed that the DNA capture efficiency of the Ppy nanochip structure was similar to that of the nanowire structure. A voltage of 1.3 V was applied to the captured DNA for three minutes, thereby effectively releasing the DNA.

Next, the captured cfDNA is detached and released by applying an electric signal.

Here, in the case of the nanostructure, an electric signal of about −1.3 to −1.0 V was applied for four to six minutes to release the cell free DNA (cfDNA) from the conductive polymer, followed by being subjected to application of an oxidation voltage of 1.3 to 1.8 V, most preferably 1.3 V. In addition, in the case of the flat structure, an electric signal of about −1.3 to −1.0 V was applied for four to six minutes to release the cfDNA, followed by being subjected to application of an oxidation voltage of 1.3 to 1.8 V, most preferably 1.5 V.

In addition, the released cfDNAs could be observed using a label, etc.

A specific label or detectable group used in a test may be any label which is detected by spectroscopic, photochemical, biochemical, immunochemical, electrical, optical, or chemical means and has detectable physical or chemical characteristics. Accordingly, the label is any composition which may be detected by spectroscopic, photochemical, biochemical, immunochemical, electrical, optical, or chemical means.

Examples of a useful label include AlexaFluor, a fluorescent dye (Invitrogen), a magnetic bead (e.g., Dynabeads™), a fluorescent dye (e.g., fluorescein isothiocyanate, Texas red, rhodamine, etc.), radioactive labels, other imaging agents (e.g., microbubble (for ultrasonic waves)), enzymes (e.g., horseradish peroxidase, alkaline phosphatase used commonly in ELISA, etc.), and colorimetric labels (e.g., colloidal gold or colored glass), or plastic (e.g., polystyrene, polypropylene, latex, etc.) beads.

Means for detecting a label are known in those skilled in the art. For example, a label is a fluorescence label, the fluorescence label may be detected by exciting fluorescent color with a suitable optical wavelength and detecting generated fluorescence. Fluorescence may be visually detected by a film for camera, an electron detector (e.g., a charge coupling device (CCD) or a photomultiplier tube), etc.

The method of the present invention has the following advantages.

(i) cfDNA is easily attached and isolated: cfDNA, preferably ctDNA, may be easily attached only by applying a positive voltage to a conductive polymer for a short time, e.g., about one minute, to treat DNA in a sample and allowing reaction at about 1 V for about 30 seconds. In addition, when a voltage of about −1.3V is applied for about five minutes to collect attached DNA, 90% or more of the attached DNA may be collected. Accordingly, DNA may be attached to a sample and detached therefrom without the use of a conventional positively charged polymer or other molecules.

(ii) An attachment rate is superior and a detection method is efficient: In a free-standing nanowire structure, a surface of each nanowire column may be modified and thus a wide surface area may be provided, thereby greatly increasing adhesion to ctDNA. In addition, since the nanowire structure, as a conductive structure, responds only to external electrical stimulation, attached ctDNA may be detached only by an electric signal.

(iii) As well as DNA present in blood, DNA present in body fluids such as saliva, urine, and excrement, may also be isolated.

(iv) Small DNA fragments may be detected.

<Capture Kit>

In another aspect, the present invention relates to a kit for detecting or isolating circulating cell-free DNA (cfDNA) including the structure.

In an embodiment, provided is a DNA detection device (kit) including a solid substrate that includes a structure surface-modified to have positive charge, an electrode for applying voltage to the structure in the solid substrate, and a measuring part for measuring electric signals generated when a sample containing DNA passes through the structure.

As needed, a chamber for storing a sample which is connected to a solid substrate and in which a sample applied to the structure is stored may be further included.

The DNA detection device (kit) includes a reaction reagent for measuring a cfDNA amount in a biosample. A cfDNA amount in a biosample may be measured with, without being limited to, any means generally known in the art, such as nucleic acid dyes (e.g., intercalator, etc.).

Non-restrictive examples of the DNA intercalator that may be used to measure a cfDNA amount and included in the kit according to the present include berberine, ethidium bromide, proflavine, daunomycin, doxorubicin, thalidomide, Sybr Green, Sybr Gold, and PicoGreen.

<Other Uses>

In another aspect, the present invention relates to a method of providing an information to diagnose the onset of and a prognosis for cancer in a subject, the method including detecting and isolating circulating tumor DNA (ctDNA) and analyzing the same.

In addition, the present invention relates to a method of diagnosing the onset of and a prognosis for cancer in a subject, the method including detecting and isolating circulating tumor DNA (ctDNA) and analyzing the same.

In the present invention, the term "cancer" represents or refers to a physiological status characterized by atypical and uncontrolled cell growth in mammals. Cancer to be diagnosed may be selected from the group consisting of carcinoma, lymphoma, blastoma, sarcoma, liposarcoma, neuroendocrine tumor, mesothelioma, schwannoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, brain cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney and renal cancer, prostate cancer, vulval cancer, thyroid cancer, hepatic carcinoma, anal carcinoma, penile carcinoma, testicular cancer, esophageal cancer, biliary tract, and head and neck cancer. Preferably, the cancer is breast cancer, lung cancer, gastric or stomach cancer, liver cancer, or pancreatic cancer.

The method of the present invention may be used to evaluate the cancer patients and persons having cancer risks. Any method of the diagnosis or prediction methods disclosed in the present invention may be used to provide one or more cancer indicators, e.g., to diagnose or predict the presence or absence of cancer cells or other diseases. To accomplish this, the amount (concentration), a copy number, or sequences of ctDNA in a sample may be analyzed and characterized.

Analysis and characterization of ctDNA may be carried out for a predetermined time at various intervals to evaluate disease development and status in a subject. For example, to follow the development and status as a function of time, the analysis and characterization may be carried out at a regular interval such as every day, per two days, three days, one week, two weeks, one month, two months, three months, six months, or one year.

With regard to the amount (concentration) or copy number of ctDNA over time, any increase of two, five, or ten folds or more indicates a deteriorated prognosis for a patient and is an initial indicator indicating a need for a treatment change in a patient. Similarly, any increase of two, five, ten folds or more indicates that a patient should be subjected to an additional test, such as imaging, to further evaluate a prognosis for and a reaction to a treatment.

Any reduction in the amount and copy number of ctDNA over time indicates stabilization of a disease and a responsiveness of a patient to a treatment and is an indicator indicating that the treatment does not need to be changed. In a person having cancer risk, a rapid increase in detected ctDNA amount (concentration) or copy number may provide an early warning indicating that a tumor in the patient has developed or proliferated and may provide an early diagnosis.

In the method, another analysis may be performed to provide another clinical assessment. For example, other than an image analysis, a gene expression analysis and PCR technique, e.g., gene chip analysis for obtaining information about the type of tumor from which ctDNA is derived, metastatic status, and malignancy, and multiplexing using primers specific to specific cancer may be used. In addition, to obtain additional information for characterizing cancer of a patient, a cell size analysis, DNA or RNA analysis, proteomic analysis, or metabolome analysis may be performed. In various aspects, the analysis includes PCR multiplexing that uses antibodies derived from primers specific to one or more of the following markers or the primers: EGFR, HER2, ERCC1, CXCR4, EpCAM, E-cadherin, mucin-1, cytokeratin, PSA, PSMA, RRM1, androgen receptors, estrogen receptors, progesterone receptors, IGF1, cMET, EML4, or leukocyte-associated receptors (LAR).

In addition, the present invention may provide sufficient data for determining the response of a subject to a specific therapy regimen or the effects of candidate drugs in a cancer treatment.

For example, when a medicinal treatment to a patient is conducted, it is possible to measure the effects of the medicinal treatment using the method of the present invention. For example, a sample collected from a patient before a medicinal treatment and one or more cell samples collected from the patent at the beginning of the medicinal treatment or after the medicinal treatment may be treated using the method of the present invention. By comparing analysis results of the respectively treated samples, the effects of the medicinal treatment or the response of the patient to the medicine may be determined. In this manner, an early confirmation against failed compounds or a detection of promising compounds may be performed.

In addition, the present invention may provide a method of determining candidate subjects for a specific clinical test. For example, to determine whether a particular therapeutic remedy can be successfully performed by analyzing detected candidate ctDNA, the presence or absence of a particular marker may be determined.

In addition, a ctDNA analysis during clinical tests may provide information about whether a patient responds to the test drug or not. Here, a practically absent change or a reduction in the investigated ctDNA indicates responsiveness of the patient to the test drug, and an increase in the ctDNA indicates poor responsiveness. The information is an initial indicator for drug effects and may be used as a secondary endpoint by researchers in a clinical test.

As described above, the present invention includes all of various uses of the three-dimensional nanostructure composed of the surface-modified conductive polymer in detecting or isolating circulating cell-free DNA (cfDNA). Accordingly, the present invention provides useful information about the onset diagnosis of and a prognosis for cancer using, particularly, circulating tumor DNA, thus being very useful in selectively and individually treating cancer.

EXAMPLES

Example 1. Experimental Materials and Methods to Synthesize Nanowire Structure 1-1. Manufacture of Ppy-Coated Au NWs (Ppy/Au NWs)

An approximately 150-nm-thick Au layer was deposited onto one surface of the AAO template (Whatman; pore diameter, 100 nm) by employing the conventional thermal evaporation technique. Au nanowires were electrochemically grown within the pores of the Au-backed AAO membrane by using a gold-plating solution (Orotemps 24 RTU Rack) and applying cyclic voltammetry in the potential range of $-1.1$-$0$ V at a scan rate of 100 mV/s.

All electrochemical experiments were conducted using a potentiostat/galvanostat (BioLogic SP-150) in 3-electrode cells, in which Ag/AgCl, platinum wire, and the designed platform were employed as reference, counter, and working electrodes, respectively. After fixing on the indium tin oxide (ITO) surface by using a conductive carbon paste, the generated membrane was dissolved in an aqueous NaOH solution (2 M) for 4 h to remove the AAO template; this ultimately produced vertically aligned arrays of Au NWs of distinct lengths.

To prepare Ppy-coated Au NWs, we performed electrochemical deposition of Ppy on freestanding Au NWs in an aqueous mixture of 0.1 M pyrrole and 0.01 M poly(sodium 4-styrenesulfonate) (PSS) by applying chronoamperometry (CA) at 0.8 V (vs. Ag/AgCl) for 20 s. The resulting Ppy/Au NWs were rinsed several times with water and incubated in Tris-HCl (pH 7.5) for the electrochemical overoxidation of the thin layer of Ppy by applying 1.8 V (vs. Ag/AgCl) for 2 min.

As such, a conductive polymer, Polypyrrole (Ppy), was manufactured as nanowires having various lengths and diameters. Subsequently, as illustrated in FIG. 1, the conductive nanowire structure was surface-modified by an electrical method and thus positively or negatively charged, thereby facilitating attachment and isolation of cfDNA having negative charge present in blood.

1-2. Sample Collection and Preparation

Whole blood was collected in Vacutainer tubes containing the anti-coagulant EDTA by using procedures approved by the NCC Institutional Review Board. Plasma was separated using a refrigerated centrifuge (3000×g, 10 min). To evaluate the capture and release efficiency of our Ppy/Au NW platforms, artificial blood samples that were prepared by the ex vivo spiking of DNA ladders (50 ng) into 200 μL of plasma obtained from healthy donors were used. For clinical applications, blood samples from three healthy volunteers and 17 patients with breast and lung cancers were collected.

1-3. DNA Capture and Release

Before evaluating their DNA-capture efficiency, the over-oxidized Ppy/Au NWs were immersed in blood samples for 30 min at room temperature in order to promote DNA interaction with individual nanowires: the samples were i) artificial samples containing spiked DNA molecules (250 ng/ml) in human plasma or ii) unprocessed plasma samples (0.2 to 1 ml) obtained from 3 healthy donors and 17 cancer patients Next, immediate DNA capture was performed by applying 1.0 V (vs. Ag/AgCl) for 30 s. Then, to release the captured DNA, electrical stimulation of Ppy/Au NWs was performed at −1.3 V (vs. Ag/AgCl) for 5 min. The captured and released DNA was quantified by using the PicoGreen assay.

The obtained DNA was measured spectrophotometrically at 260 and 280 nm, and the A260/A280 ratio was used to assess the purity of the captured and released DNA. The interactions between Ppy/Au NWs and DNA were visualized by examining PicoGreen fluorescence under a Zeiss LSM 710 confocal microscope.

1-4. PCR and Gel Electrophoresis

The sequences of all primers used are summarized in Table 1 below (Macrogen, Korea)

TABLE 1

| Primer Name | Primer sequence (5' → 3') | |
|---|---|---|
| K-Ras forward primer | ACTGAATATAAACTTGTGGTA GTTGGACCT | SEQ ID NO: 1 |
| K-Ras reverse primer | ACTCATGAAAATGGTCAGAGA AACCTTTAT | SEQ ID NO: 2 |
| EGFR (Exon 19) forward primer | GCACCATCTCACAATTGCCAG TTA | SEQ ID NO: 3 |
| EGFR (Exon 19) reverse primer | AAAAGGTGGGCCTGAGGTTCA | SEQ ID NO: 4 |
| P53 forward primer | CAGCACATGACGGAGGTTG | SEQ ID NO: 5 |
| P53 reverse primer | TCATCCAAATACTCCACACGC | SEQ ID NO: 6 |
| GAPDH forward primer | GGAGCGAGATCCCTCCAAAAT | SEQ ID NO: 7 |
| GAPDH reverse primer | GGCTGTTGTCATACTTCTCA | SEQ ID NO: 8 |

DNA ladders (low: 10 to 100 bp; middle: 100 bp to 2 kb; high: 3.5 to 21 kb) were purchased from Bioneer, Korea. All PCR amplifications were performed in a GeneAmp PCR system 9600 (Perkin Elmer, Norwalk, Conn., USA) in a final reaction volume of 20 μL that contained template DNA, 2 oligonucleotide primers (5 pM), 200 mM of each dNTP, 10 mM Tris-HCl (pH 7.5), 50 mM KCl, 1.5 mM MgCl2, 0.1% (w/v) gelatin, and 1 U of Taq DNA polymerase (Perkin Elmer).

PCR amplification consisted of 45 cycles of denaturation (94° C., 30 s), annealing (64° C., 30 s), and elongation (72° C., 1 min). PCR products were electrophoresed on 2% agarose gels and stained with ethidium bromide to visualize their presence under a UV transilluminator.

1-5. QIAamp Circulating Nucleic Acid Kit cfDNA was extracted from 1 ml of plasma by using the QIAamp circulating nucleic acid kit (Qiagen). Briefly, plasma samples were lysed using proteinase K and a lysis buffer, and then the circulating nucleic acids were bound to the silica membrane by applying vacuum pressure. DNA fragments were recovered from the membrane after several washing steps.

1-6. Digital PCR

EGFR mutation in cfDNAs was examined by using PrimePCR ddPCR mutation assay kits for EGFR L858R and Exon 19 deletion (p.E746-A750del) on a QX200 ddPCR system (BioRad, Hercules, Calif., USA). Water-oil emulsion droplets were generated from PCR mixtures that contained 8 μL of cfDNA, 10 μL of ddPCR supermix, and 2 μL of target primers and probes. After generating the droplets, PCR was performed in a thermal cycler. Positive droplets, which contained at least one copy of the amplified DNA, could be detected by the droplet reader for a fluorescence analysis.

1-7. Mutation Test for EGFR Gene

The EGFR gene status in the primary tumor tissue was examined using the PCR-direct sequencing method. Genomic DNA was extracted and amplified using specific primers for Exons 19 and 21 of the EGFR gene. PCR products were sequenced using the BigDye terminator cycle sequencing kit and analyzed using an ABI PRISM 3100 DNA analyzer (Applied Biosystems, Foster City, Calif., USA).

1-8. Manufacture of Nanowire Structures Using Various Conductive Polymers

Nanowire structures were manufactured using various conductive polymers, such as polyaniline (PANI) and polythiophene (PEDOT), other than polypyrrole. In particular, a polyaniline (PANI) solution was prepared through addition of 1 M sulfuric acid and 0.1 M aniline, and 0.1 M lithium perchlorate (LiClO$_4$) and 0.1 M 3,4-ethylenedioxythiophene (EDOT) prepared from an acetonitrile solution were mixed to prepare a polythiophene (PEDOT) solution. ITO glass was bound to a cell battery and then each of the prepared polymer solutions was applied thereto in an amount of 1 ml. Subsequently, electrical stimulation of 1.5 V was applied for five minutes to perform polymerization. Subsequently, the cell battery was washed with distilled water three times and then immersed in a PBS solution containing 360 ng/200 μl of a middle size DNA ladder, followed by incubating for one hour. Subsequently, an electrical stimulation of 1.0 V was applied for three minutes, and then a supernatant was isolated. DNA was quantified from the isolated supernatant using PicoGreen assay.

Example 2. Evaluation of Attachment/Isolation Ability to cfDNA Using Nanowire Structure Using the feature that a surface of polypyrrole is effectively modified by electrical stimulation, concentration and isolation of cfDNA were attempted by spiking a DNA ladder in plasma. In addition, it was confirmed that cfDNA was attached/isolated in a much higher amount in a nanowire structure than a flat surface.

Figure 4A:
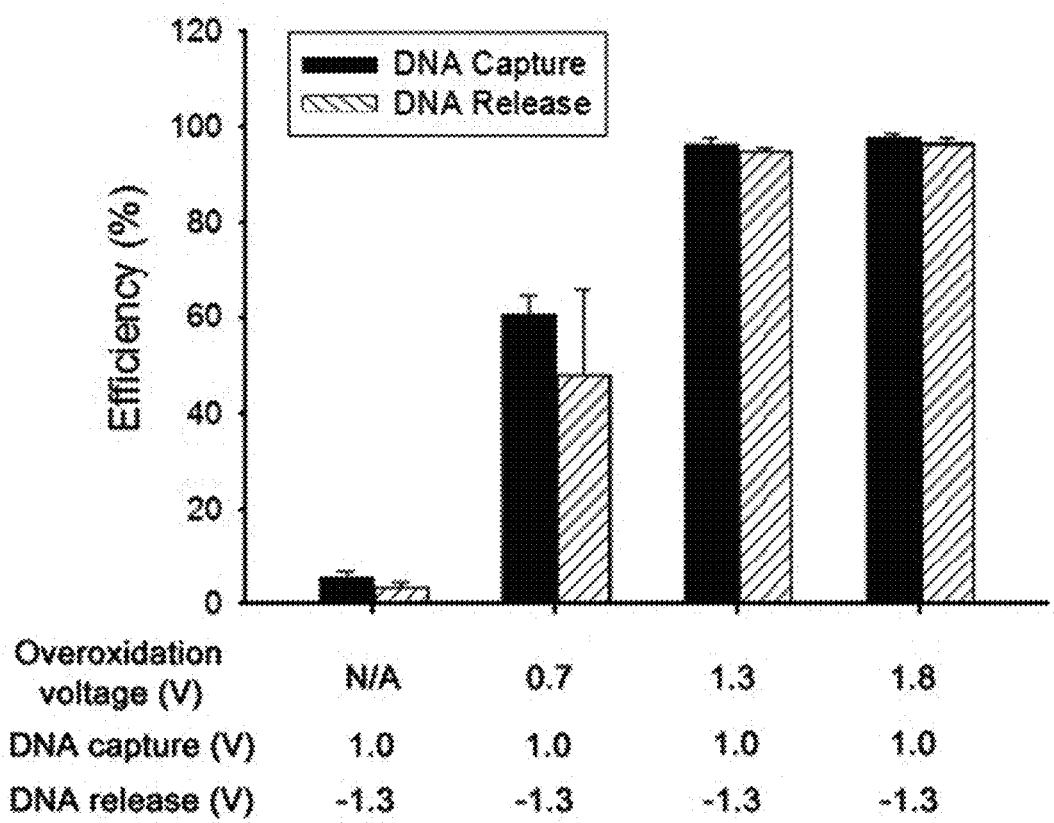
FIGS. 4A to 4F illustrate evaluation results of attachment and isolation ability of a nanowire structure of the present invention to cfDNA through the control of voltage and time.
Figure 4B:
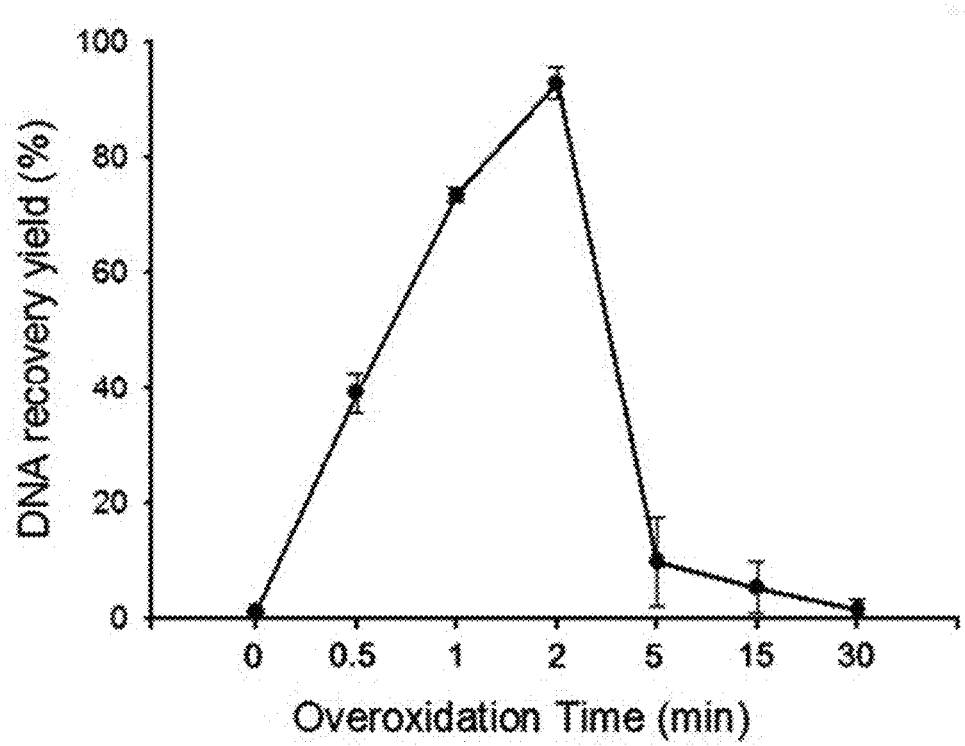
Figure 4C:
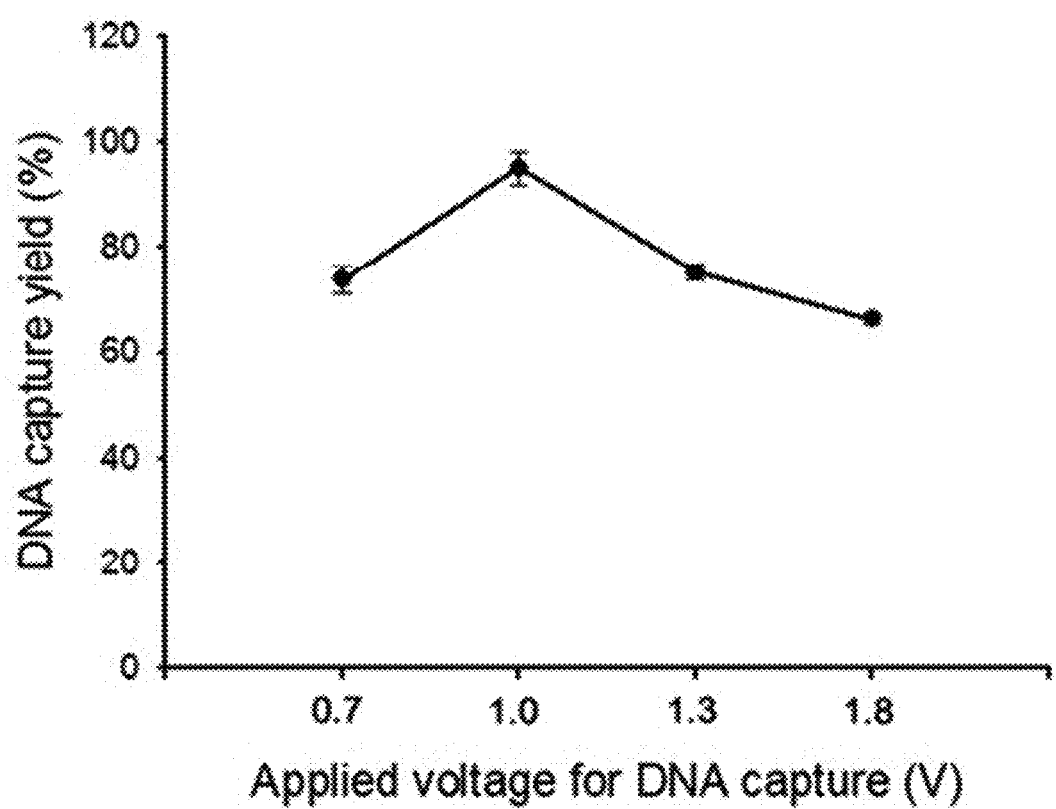
Figure 4D:
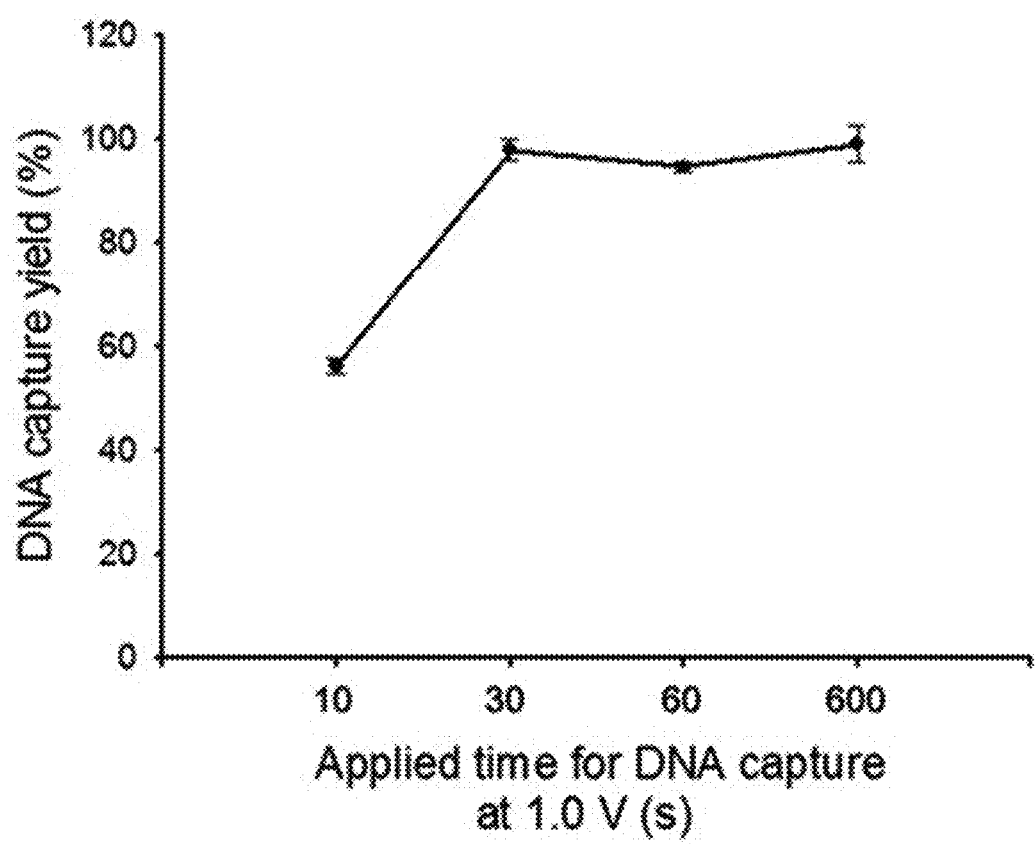
Figure 4E:
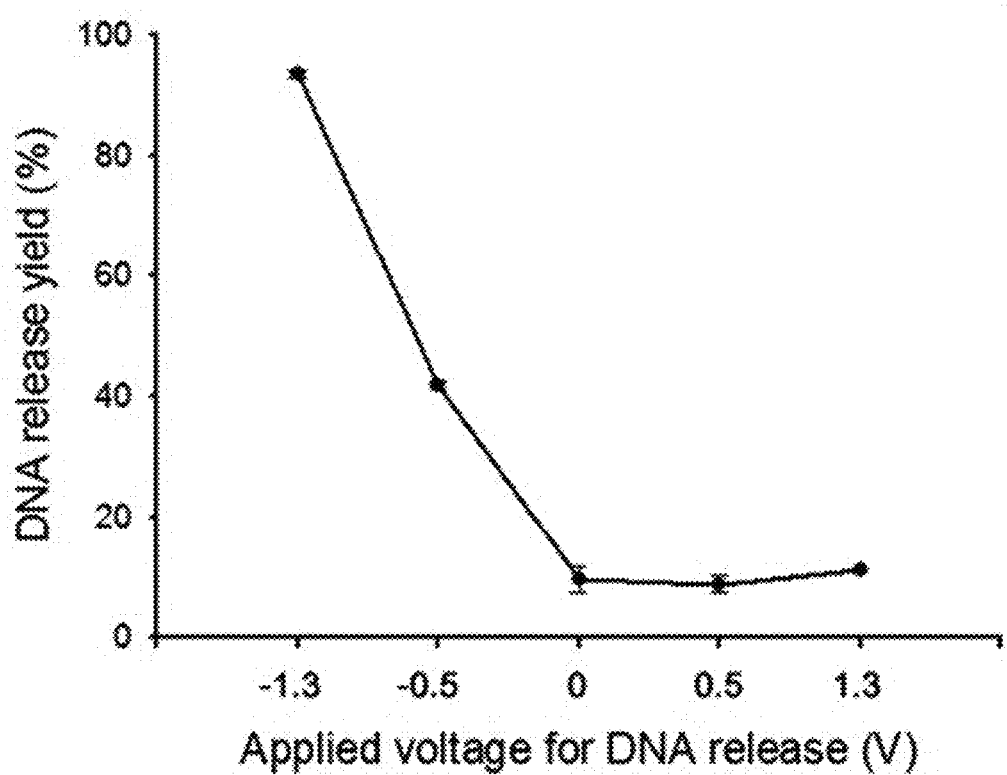
Figure 4F:
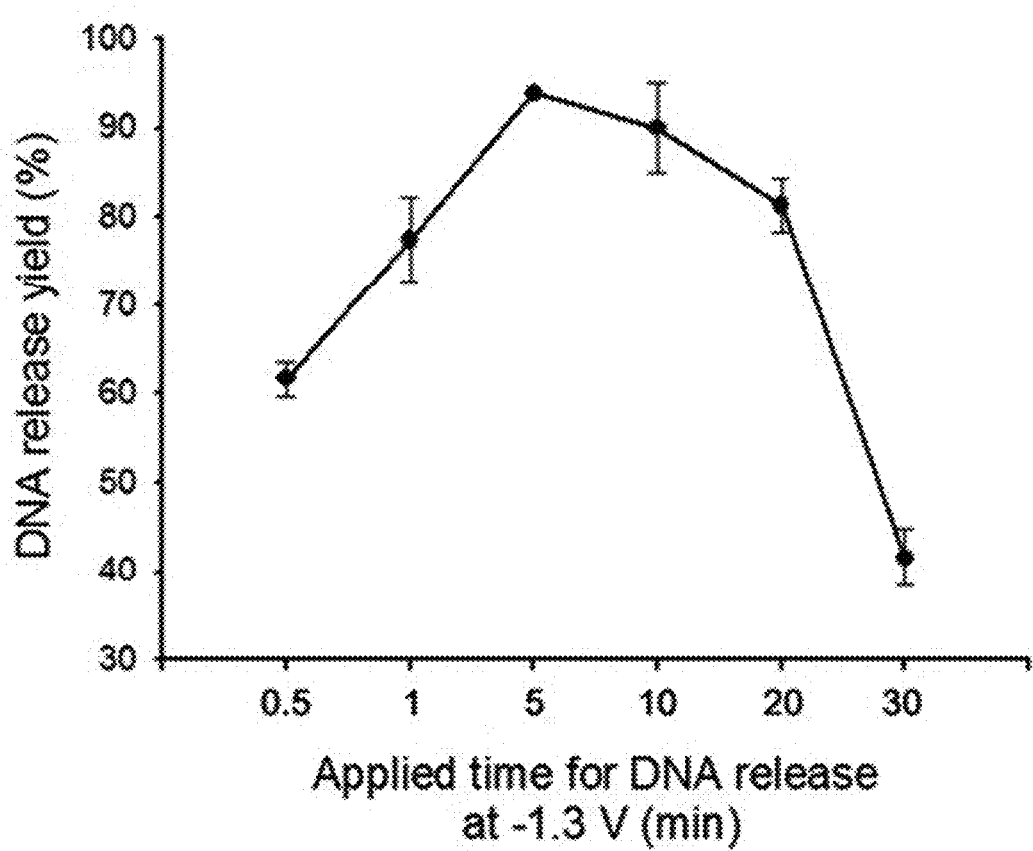

In particular, three steps are required to accomplish concentration and isolation of DNA. First, over-oxidation was carried out by applying a high voltage to a polypyrrole nanowire structure, and thus a positively charged surface was induced. Subsequently, DNA capture was attempted at 1.0 V, and then a voltage of 1.3 V was applied after washing three times, thereby releasing concentrated DNA from a surface of the nanowire structure and obtaining the concentrated DNA. As a result, it was confirmed that DNA capture efficiency increased with increasing over-oxidation voltage (see FIG. 4A), and, when a voltage of 1.8V was applied for two minutes, the highest DNA capture efficiency was exhibited (see FIG. 4B). In addition, it was confirmed that the most suitable voltage and time to accomplish efficient DNA capture were 1.0 V and 30 seconds, respectively (see FIGS. 4c and 4d). In addition, it was evaluated that the most efficient voltage and time to release the captured DNA from a surface of the nanowire structure were 1.3 V and five minutes (see FIGS. 4e and 4f).

Figure 4G:
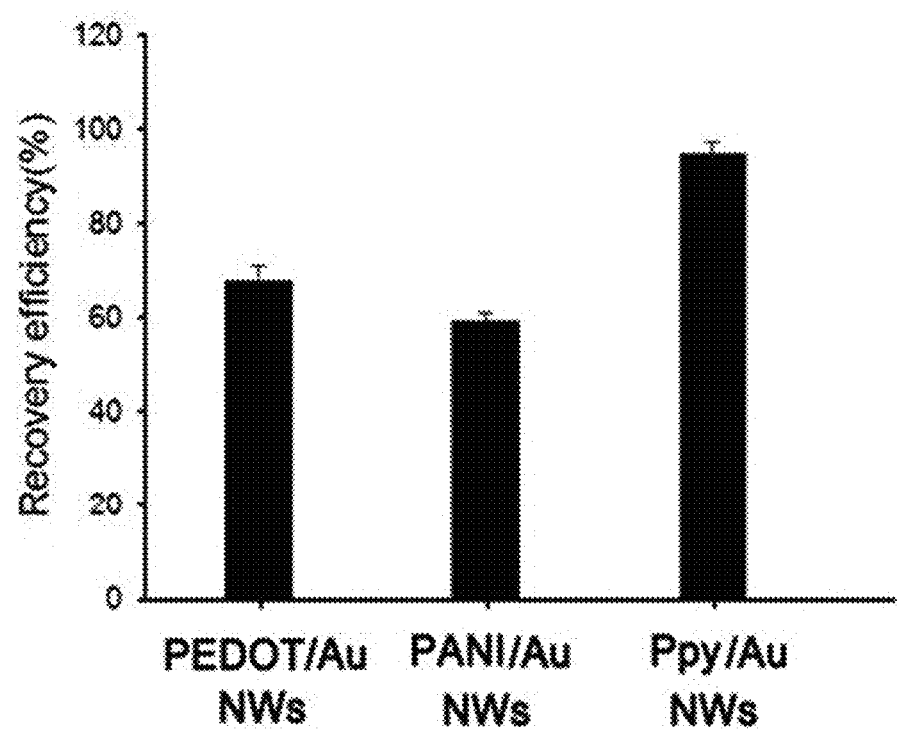
FIG. 4G illustrates a comparison result of attachment and isolation ability of nanowire structures, which use conductive polymers, polyaniline (PANI) and polythiophene (PEDOT), of the present invention to cfDNA, to that of a polypyrrole (Ppy) nanowire structure.
Figure 5A:
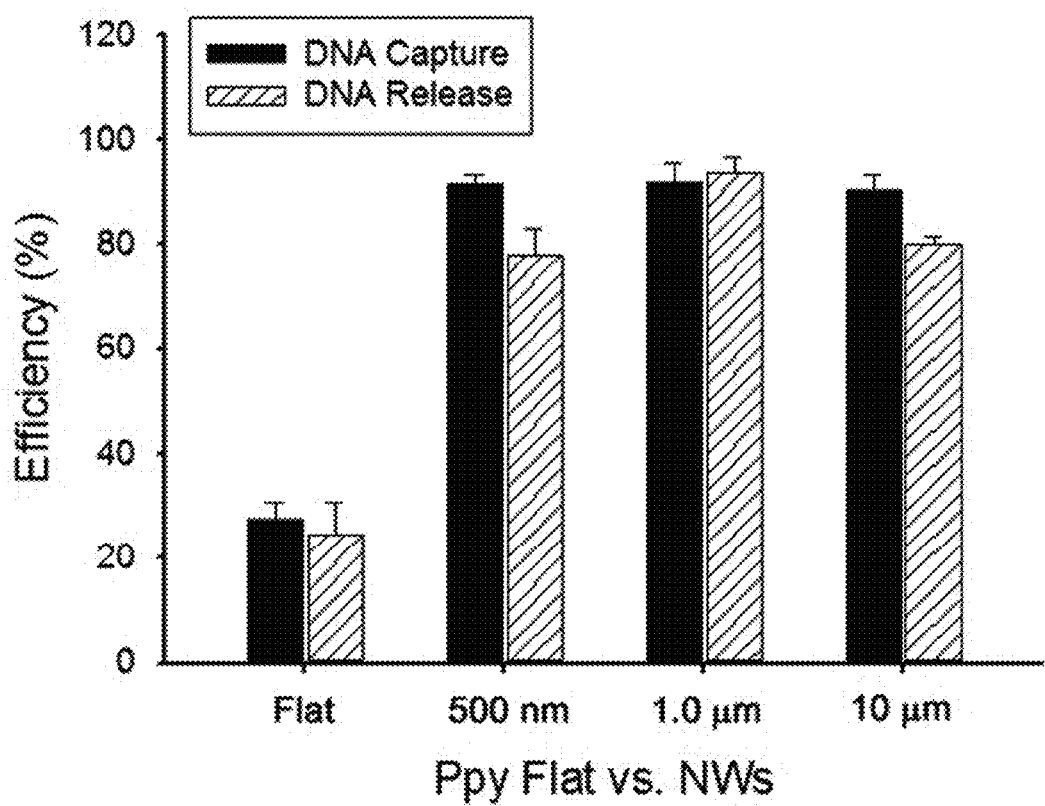
FIG. 5A illustrates evaluation results of attachment and isolation ability of a flat structure of a conductive polymer polypyrrole and a nanostructure thereof to cfDNA.
Figure 5B:
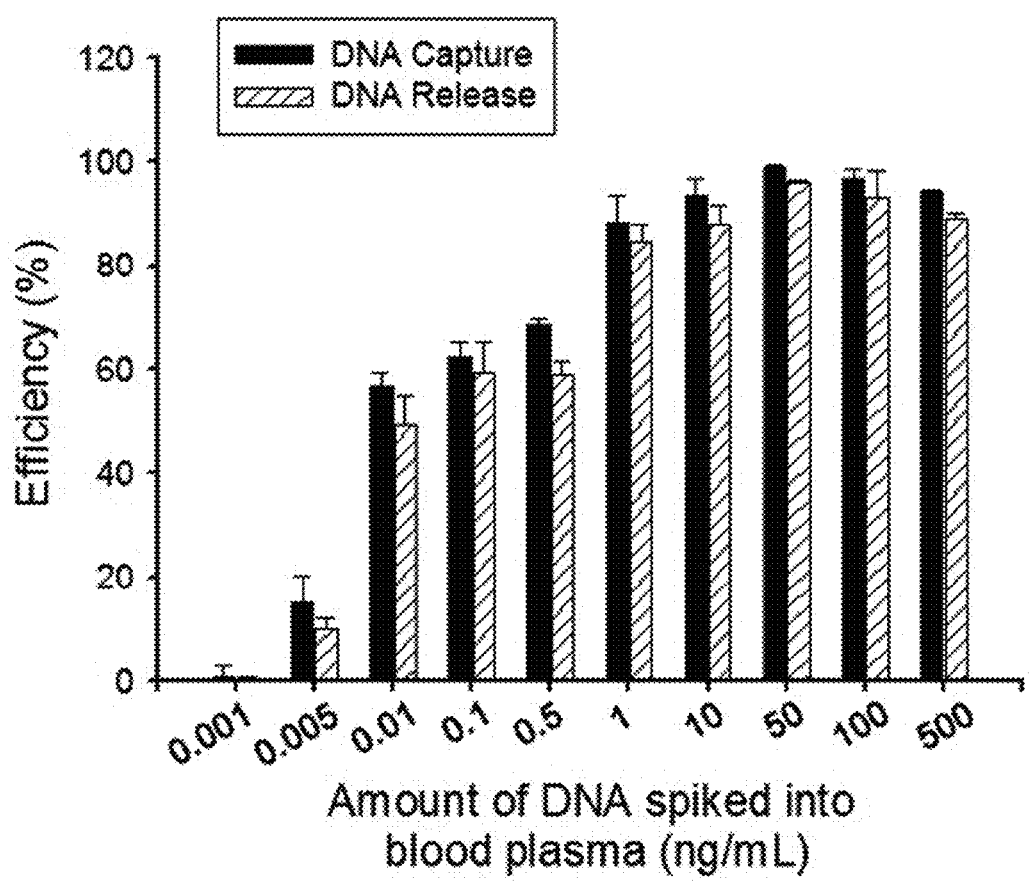
FIG. 5B illustrates concentration-based evaluation results of attachment and isolation ability of a nanostructure with a size of 1.0 µm to cfDNA.
Figure 5C:
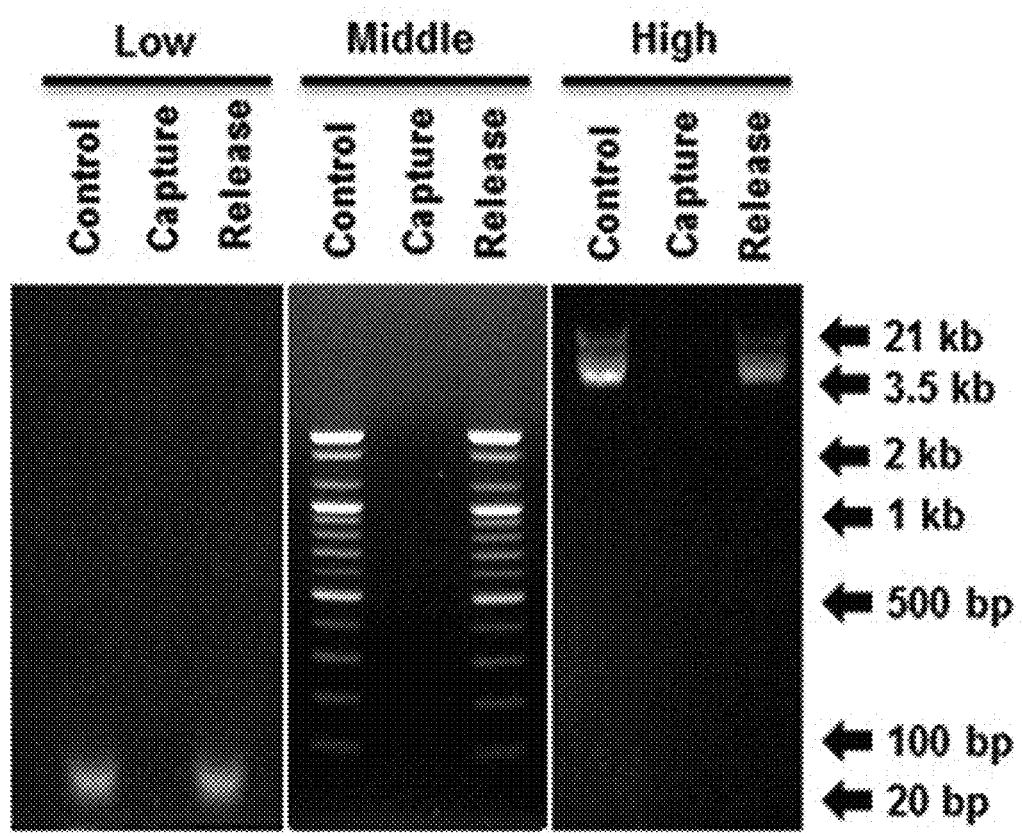
FIG. 5C and FIG. 5D illustrate evaluation results of attachment and isolation ability to cfDNA after various-size DNA was spiked into the blood plasma of a normal person.
Figure 5D:
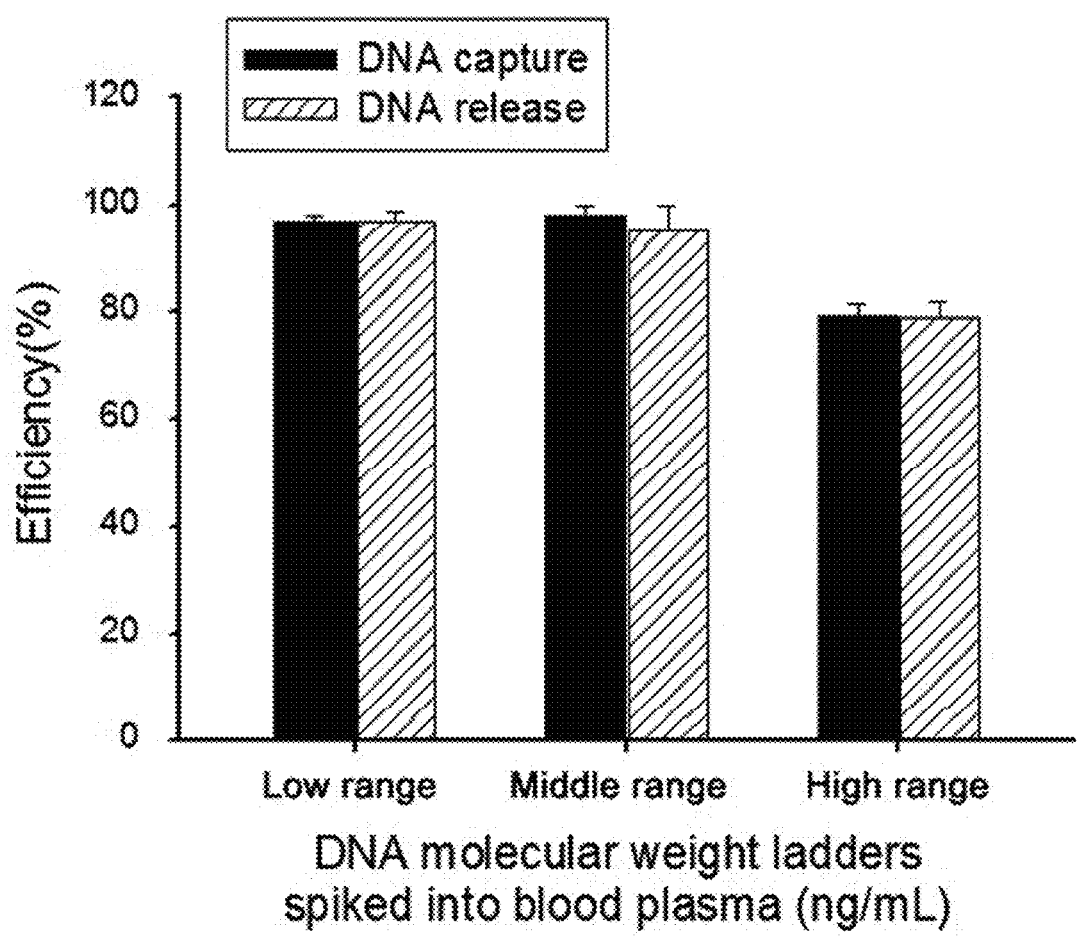

In addition, as illustrated in FIG. 4G, nanowire structures were manufactured using various conductive polymers, such as polyaniline (PANI) and polythiophene (PEDOT), other than polypyrrole, and attachment/isolation ability thereof to cfDNA was evaluated. As a result, it was observed that, when polypyrrole (Ppy) was used, the collection rate of cfDNA was highest.

In addition, the present inventors confirmed that, after spiking various-size DNA ladders in plasma, attachment and isolation ability thereto were investigated using western blotting and PICO green. Results are illustrated in FIGS. 5A to 5D. In addition, using various-molecular weight and various-concentration DNA, attachment/isolation ability thereof to cfDNA was measured.

Example 3. Evaluation of cfDNA in Blood of Breast Cancer Patient and Lung Cancer Patient Using Nanowire Structure Using blood from a breast cancer patient, cfDNA attached to a surface of the conductive nanostructure was observed using a fluorescent dye, SYBR Green/PICO Green, with a confocal microscope.

Figure 7:
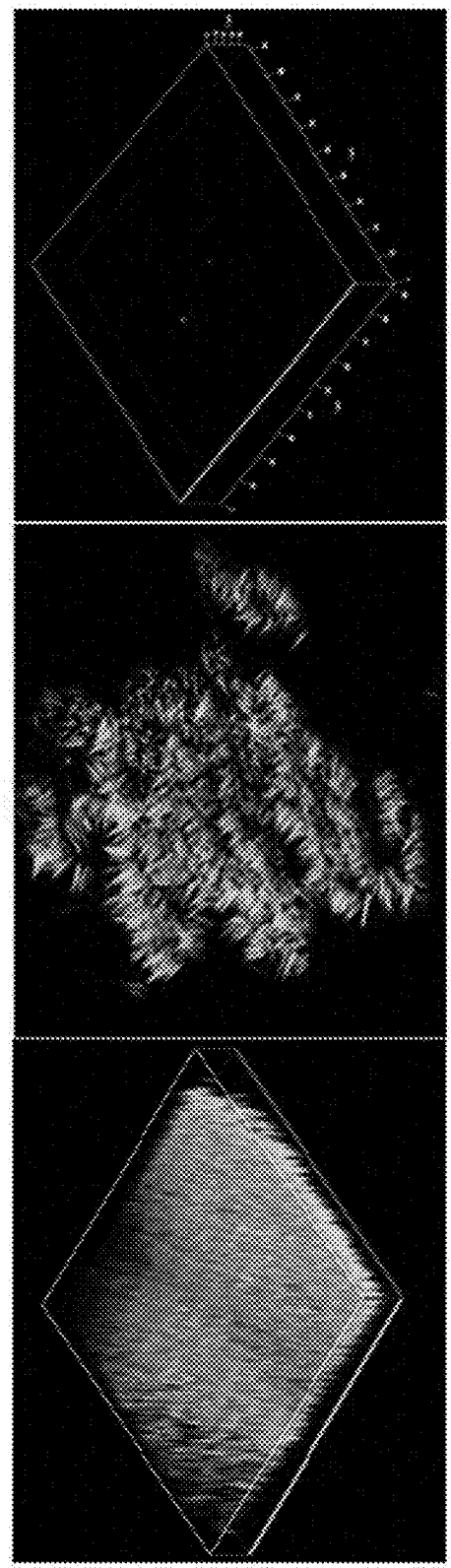
FIG. 7 illustrates confocal microscopic images of cfDNA attached (left and middle) and isolated by electrical stimulation using a polypyrrole nanostructure as a conductive polymer.

As illustrated in FIG. 7, it can be confirmed that cfDNA is completely attached to a surface of a wire when a nanowire having a length of 1.0 µm is used, and, after the application of electrical stimulation, the attached cfDNA is released and thus fluorescence is not observed.

In addition, the present inventors compared the concentrations of cfDNAs isolated by the conductive nanostructure of the present invention and Qiagen kit using blood samples from a breast cancer patient and a lung cancer patient.

Figure 6A:
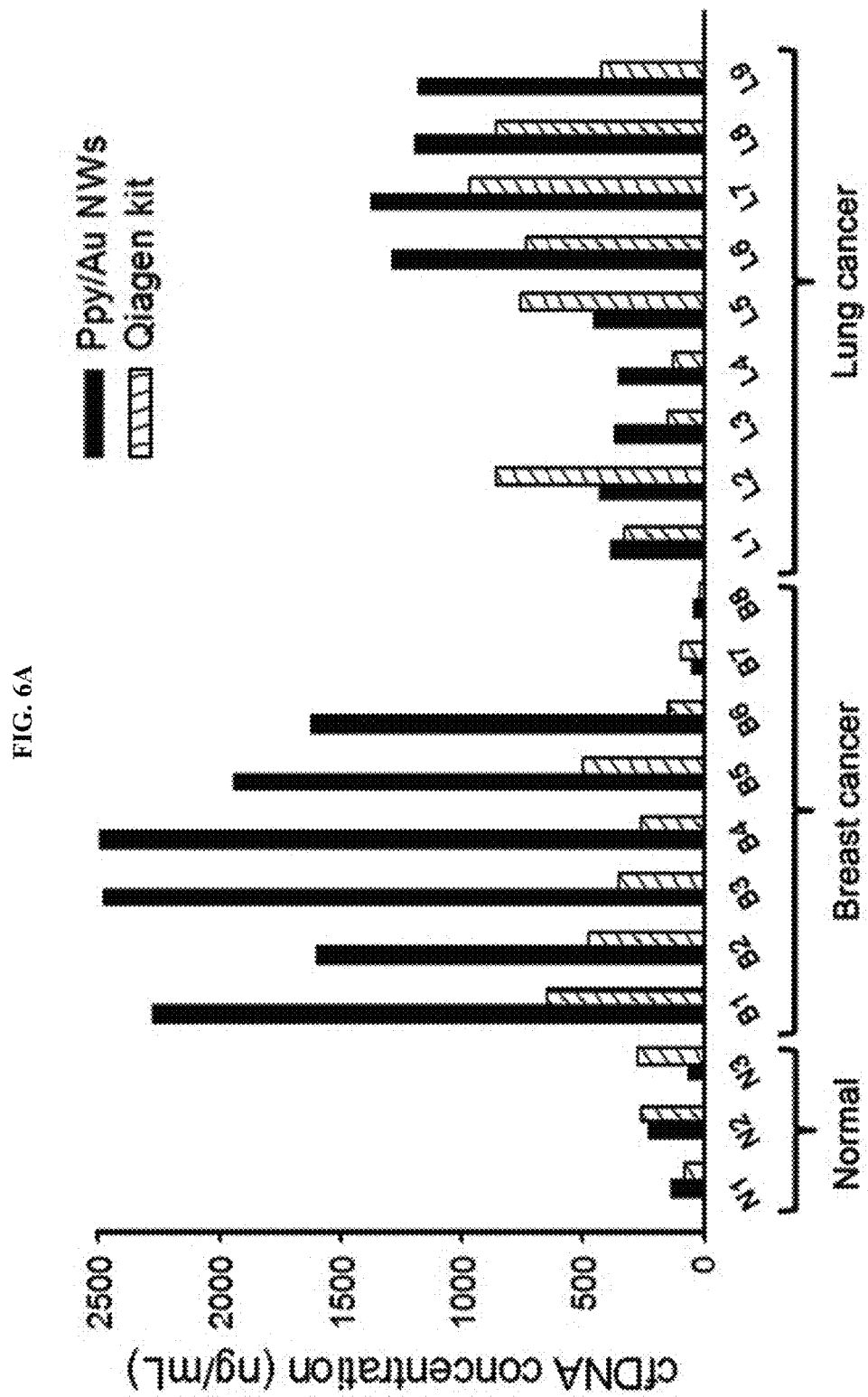
FIG. 6A illustrates, after isolating cfDNA, which is present in the blood of each of a normal person, a breast cancer patient, and a lung cancer patient, with each of a nanowire structure of the present invention and a commercially available Qiagen kit, concentration comparison results of the isolated cfDNA.
Figure 6B:
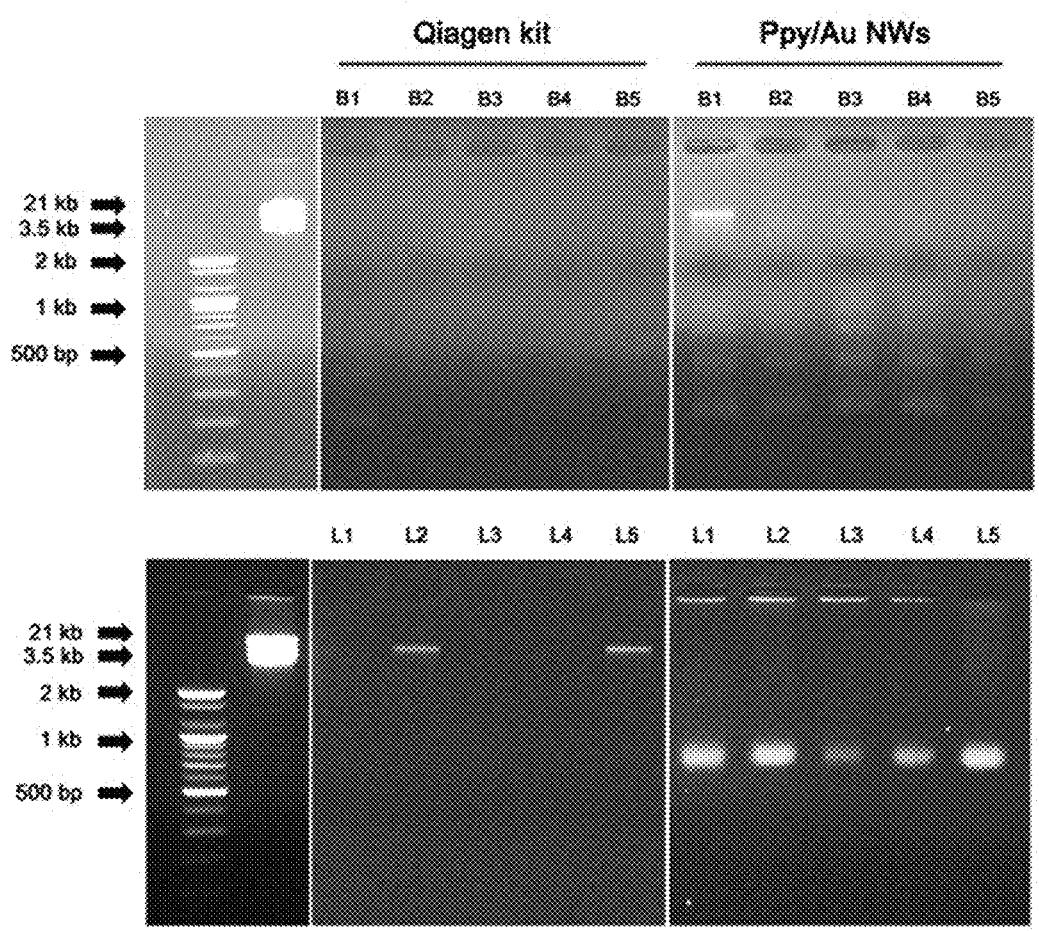
FIG. 6B illustrates, after isolating cfDNA present in the blood of each of a breast cancer patient and a lung cancer patient with each of a nanowire structure of the present invention and a commercially available Qiagen kit, investigation results of the presence or absence of the isolated cfDNA by electrophoresis. As shown in the figure, cfDNA isolated with the nanowire structure of the present invention was observed to exist in a form of small fragments that are a feature of cancer-specific ctDNA. On the other hand, cfDNA isolated by means of the commercially available Qiagen kit has a low concentration and thus was not observed in all patients.

As a result, as illustrated in FIGS. 6A and 6B, the amounts of cfDNAs from blood samples of cancer patients are up to ten fold or more with respect to the amount of cfDNA captured from blood from a normal person. In addition, when the nanostructure of the present invention is used, cfDNA is successfully isolated in a much higher amount compared to the commercially available Qiagen kit. From such data, it can be confirmed that the conductive nanowire of the present invention is effective in capturing small DNA fragments.

Figure 8:
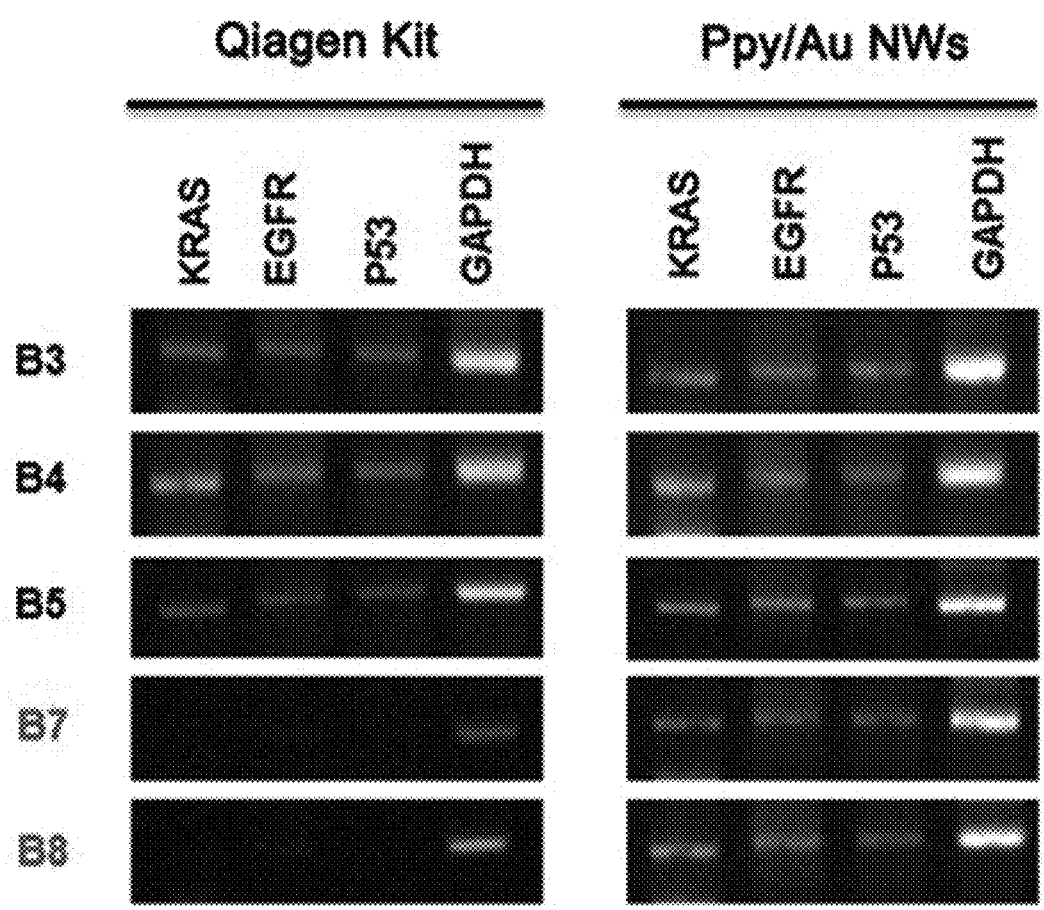
FIG. 8 illustrates, after capturing cfDNA present in the blood of each of a breast cancer patient and lung cancer patient using each of a Qiagen kit and a nanostructure, Ppy/Au NWs, and PCR amplification comparison results of the captured cfDNA.

In addition, cfDNA was captured from blood derived from a breast cancer patient using the Qiagen kit or the nanostructure, Ppy/Au NWs. Subsequently, EGFR and KRAS mutations in the patient sample were investigated using a PCR amplification method. Results are illustrated in FIG. 8. That is, EGFR and KRAS mutations may be analyzed using the nanostructure of the present invention.

In addition, cfDNA was detected from the blood from a lung cancer patient using the Qiagen kit or the Ppy/Au NWs, and then digital PCR was carried out to compare detection frequencies of EGFR mutations in the patient sample. Results are summarized in Table 2 below.

TABLE 2

| Sample | TNM staging | Primary tumor EGFR direct sequencing | Qiagen kit | | Ppy/Au NWs | |
|---|---|---|---|---|---|---|
| | | | Positive_Mutant | Positive_Wildtype | Positive_Mutant | Positive_Wildtype |
| L1 | T4N3M1 | not tested | 1 | 380 | 6 | 313 |
| | | | 7 | 472 | 6 | 288 |
| L2 | T3N2M1 | not tested | 0 | 1242 | 0 | 331 |
| | | | 0 | 1253 | 0 | 345 |
| L3 | T4N1M1 | not tested | 0 | 183 | 0 | 129 |
| | | | 0 | 176 | 0 | 128 |
| L4 | T2N2M0 | p.Glu746_Ala750del | 2 | 160 | 1 | 102 |
| | | | 2 | 170 | 1 | 139 |
| L5 | T2N3M1 | p.Glu746_Ala750del/insAlaPro | 0 | 1272 | 2 | 101 |
| | | | 0 | 1079 | 0 | 122 |

As a result, it was confirmed that the structure of the present invention had the abilities to attach and isolate DNA without being greatly affected by molecular weight or concentration. That is, it was confirmed that superior attachment to and isolation from all of low molecular weight, middle molecular weight, and high molecular weight DNA were provided and, when DNA was used at a certain concentration or more, attachment and isolation ability to DNA were not greatly affected.

As a result, the conductive nanowire of the present invention exhibits greatly increased DNA isolation results compared to the commercially available Qiagen kit. From such a result, it can be confirmed that the conductive nanowire of the present invention is much more effective in detecting ctDNA compared to the conventional Qiagen kit.

In particular, small fragment DNA, which was not detected with the commercially available product, the Qiagen kit, was detected by the polypyrrole nanowire structure of the present invention, which indicates that the polypyrrole nanowire structure may be used as a kit for cancer diagnosis.

Figure 9:
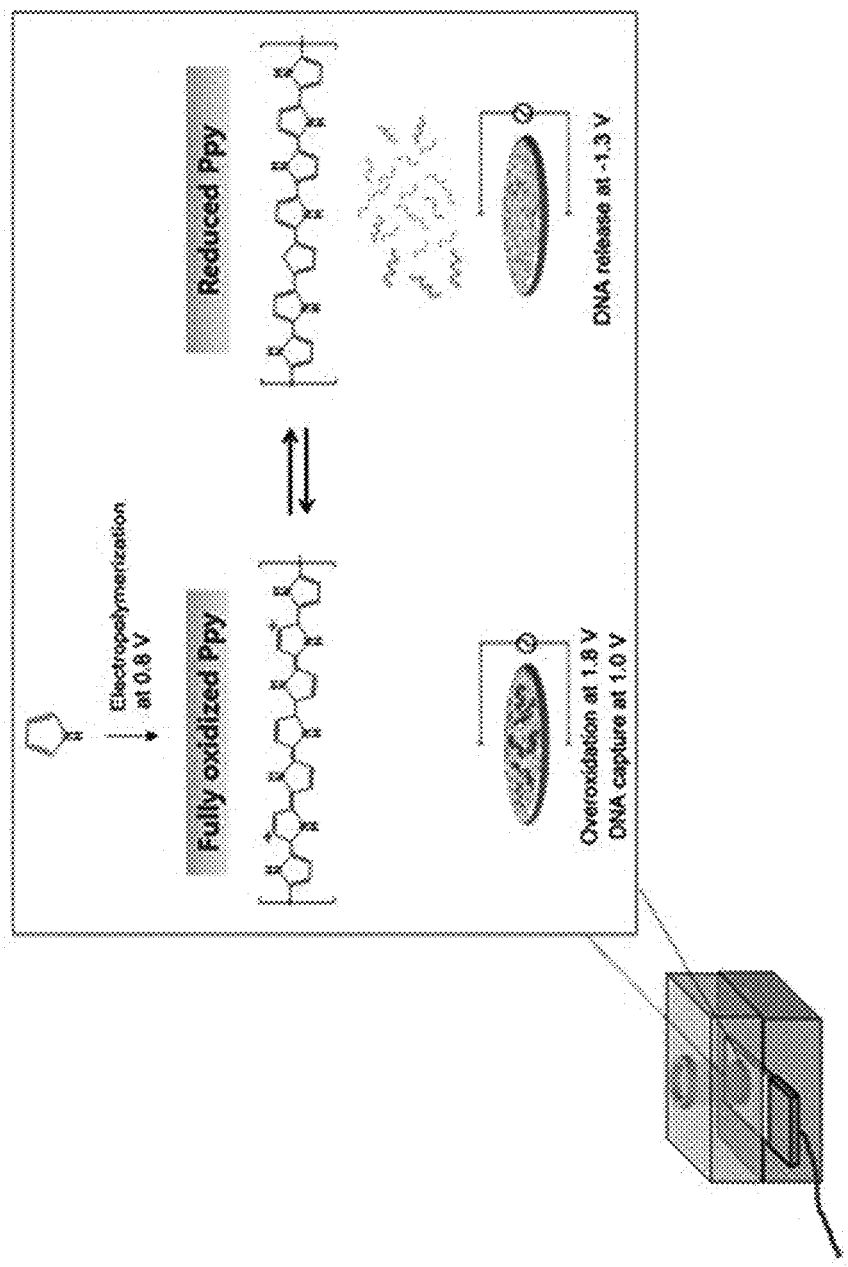
FIG. 9 schematically illustrates a method of detecting and isolating circulating cell-free DNA (cfDNA) using a Ppy nanochip structure of the present invention.

Example 4. Evaluation of Surface Roughness of Polypyrrole Nanochip Structure To investigate that a polypyrrole nanochip structure, as well as the polypyrrole nanowire structure, may also isolate circulating cell-free DNA (cfDNA) in blood, a conductive polymer having a polypyrrole nanochip structure was electrochemically surface-modified, as illustrated in FIG. 9.

Figure 10A:
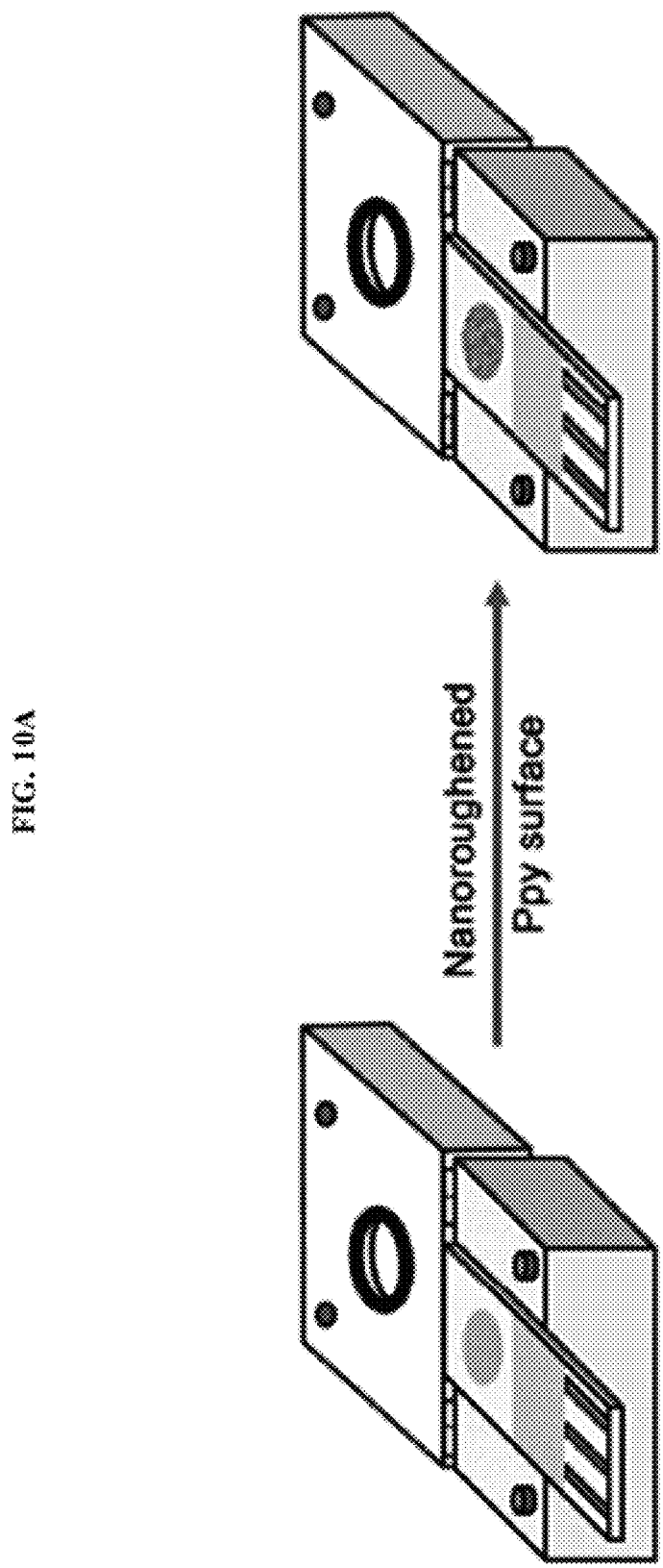
FIG. 10A illustrates a method of electrochemically coating a surface with polypyrrole.

First, to investigate the roughness of a surface of the polypyrrole nanochip structure, polypyrrole nanochip structure (Ppy-nanochip) was manufactured by electrochemically depositing polypyrrole (Ppy) on an ITO surface at 0.8 to 1.8 V (vs. Ag/AgCl) for five minutes in an aqueous mixture of 0.1 M pyrrole and 0.01 M poly(-sodium 4-styrenesulfonate) (PSS), as illustrated in FIG. 10A. All electrochemical experiments were performed using a potentiostat/galvanostat (Biologic SP-50) in three-electrode cells, where platinum wire, Ag/AgCl, and the ITO served as counter, reference, and working electrodes, respectively. Subsequently, the synthesized Ppy was rinsed twice with distilled water and incubated in Tris-HCl buffer (pH 7.5) for additional electrochemical overoxidation at 1.8 V (vs. Ag/AgCl) for 2 min. The surface roughness of the prepared Ppy platform was investigated by atomic-force microscopy (AFM) (Park Systems, XE-Bio).

Figure 10B:
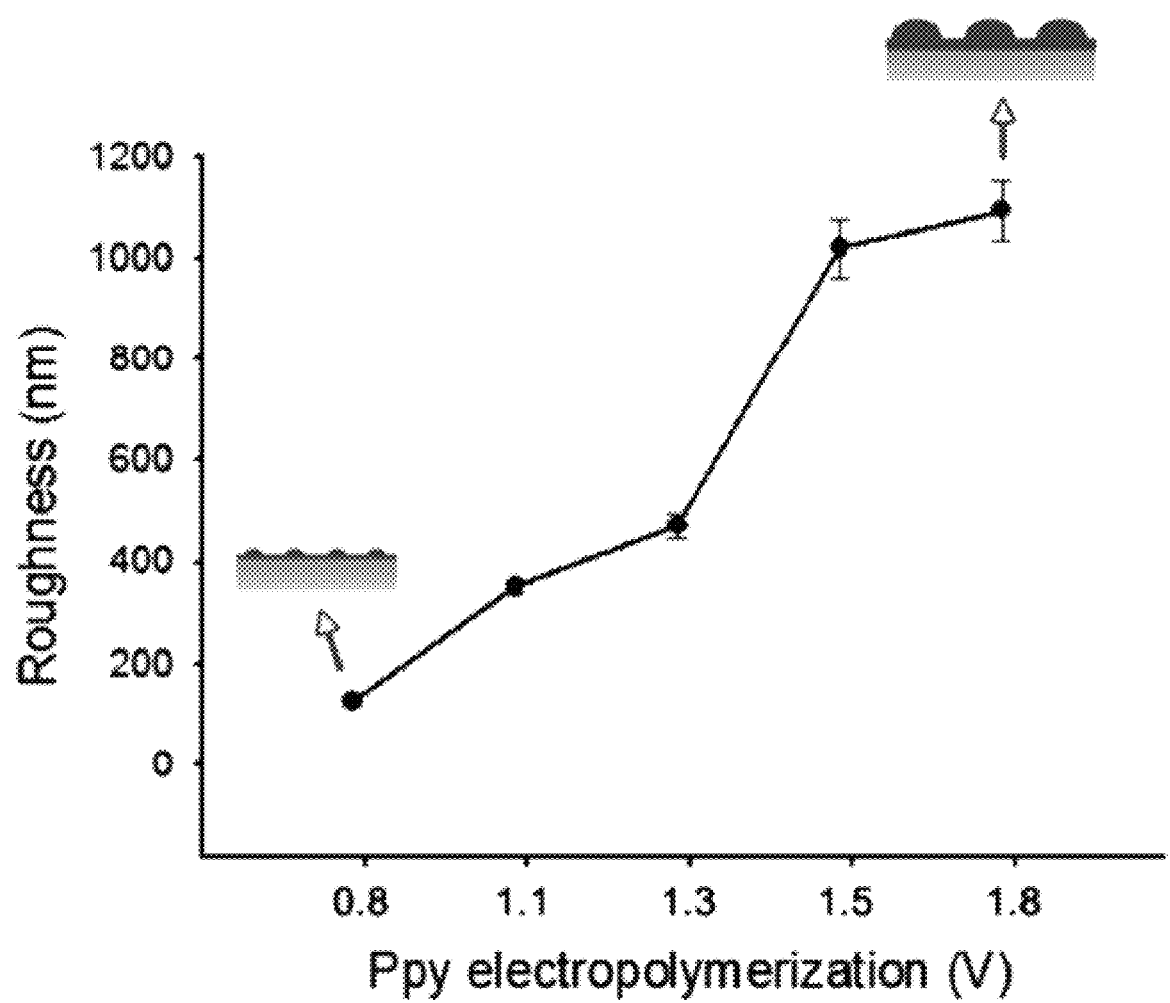
FIG. 10B illustrates roughness of a Ppy nanochip structure depending on a voltage applied to polypyrrole.
Figure 10C:
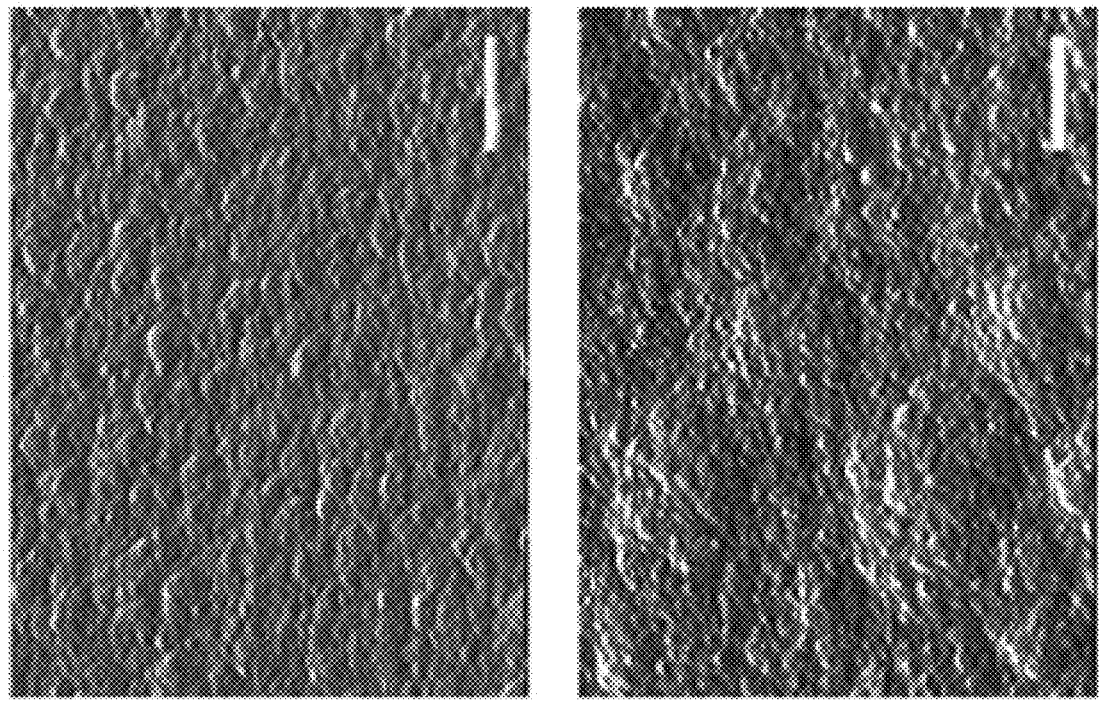
FIG. 10C illustrates surface of a Ppy nanochip structure depending on a voltage applied to polypyrrole as observed by AFM and FE-SEM.
Figure 10C:
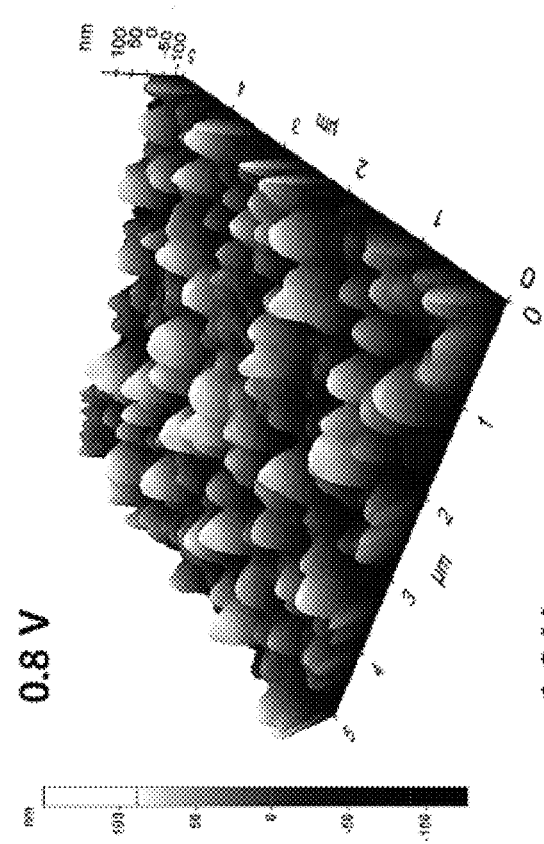
Figure 10C:
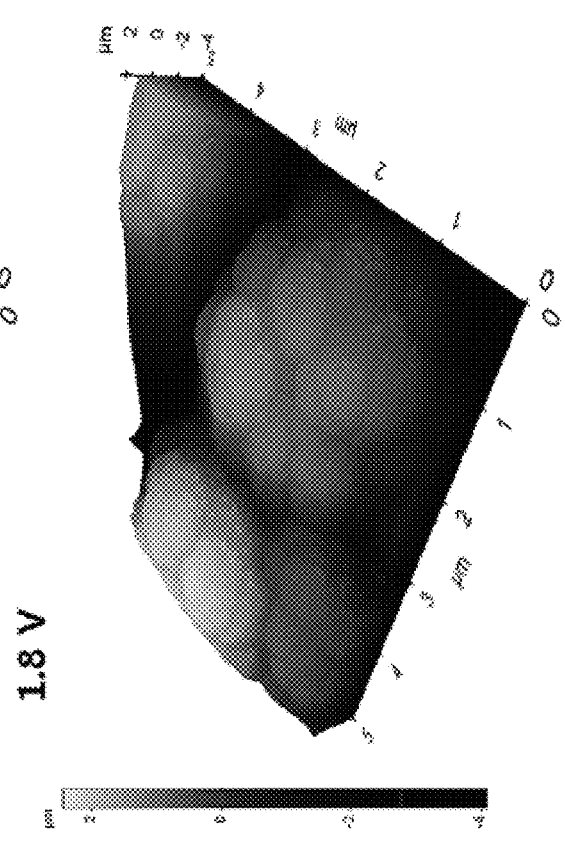

As a result, it was confirmed that, as illustrated in FIG. 10B, roughness increased with increasing high voltage applied to the polypyrrole nanochip structure. In addition, as illustrated in FIG. 10C, a surface of the Ppy nanochip structure dependent on a voltage applied to a surface of the Ppy structure was investigated using AFM and FE-SEM and the surface roughness was observed with naked eyes.

Example 5. Evaluation of Attachment/Isolation Ability to cfDNA Using Polypyrrole Nanochip Structure The procedure for DNA isolation from blood plasma using the polypyrrole nanochip structure (Ppy nanochip) includes the following steps: i) electrochemical deposition of the Ppy polymer by applying potentials at 0.8e1.8 V for 2 min to generate a nanoroughened surface; ii) overoxidation of Ppy at 1.8 V for 2 min of electrical stimulation to induce a high density of positive charges on the polymeric backbones; iii) incubation of overoxidized Ppy platform in the blood plasma for 1 h, which enhances more efficient attachment of the DNA to the Ppy platform; iv) DNA capture by exposure to 1.0 V for 3 min, immediately followed by washing the Ppy platform with 500 ml of nuclease-free water (NFW) twice to remove unbound DNA or nonspecifically bound impurities; and v) DNA collection from the Ppy nanochip in nuclease-free water (NFW) by electrical stimulation at −1.3 V for 3 min.

In addition, as described in Example 1-2, samples were collected and prepared. In the present invention, two different blood plasma were used: i) artificial blood plasma containing spiked DNA molecules (250 ng/ml) in healthy plasma; and ii) unprocessed plasma samples (100 ml to 1 ml) collected from healthy subjects or lung cancer patients. The captured and released DNA was quantified using the Picogreen assay according to the manufacturer's protocol.

Figure 11A:
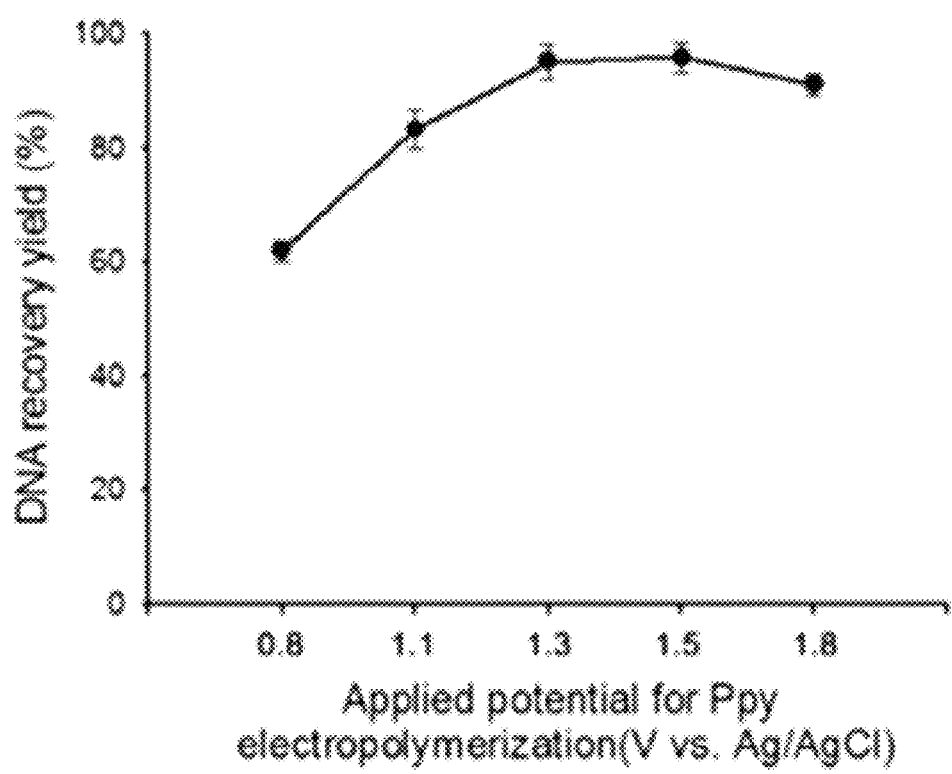
FIG. 11A illustrates that, when a surface of polypyrrole is electrochemically coated, isolation efficiency of cfDNA increases with increasing voltage applied to polypyrrole.

As a result, as illustrated in FIG. 11A, a capture amount of cfDNA, which is present in blood, and cfDNA isolation efficiency increase with increasing voltage applied to polypyrrole, when a surface of polypyrrole is electrochemically coated. In addition, it was confirmed that, when the polypyrrole nanochip structure was manufactured at a relatively low voltage of 0.8 V, very smooth surface was observed, and thus, DNA capture and release ability was not greatly improved. However, it was confirmed that, when a flat Ppy film was manufactured through an electropolymerization process, the roughness of the flat Ppy surface greatly increased upon application of a high voltage of 1.8 V, and thus, DNA collection was facilitated. From these results, it can be confirmed that the surface roughness of the nanostructure increases a volumetric area relative to a surface, as well as interaction with DNA, thereby providing sites to which a large amount of DNA can be attached.

Figure 11B:
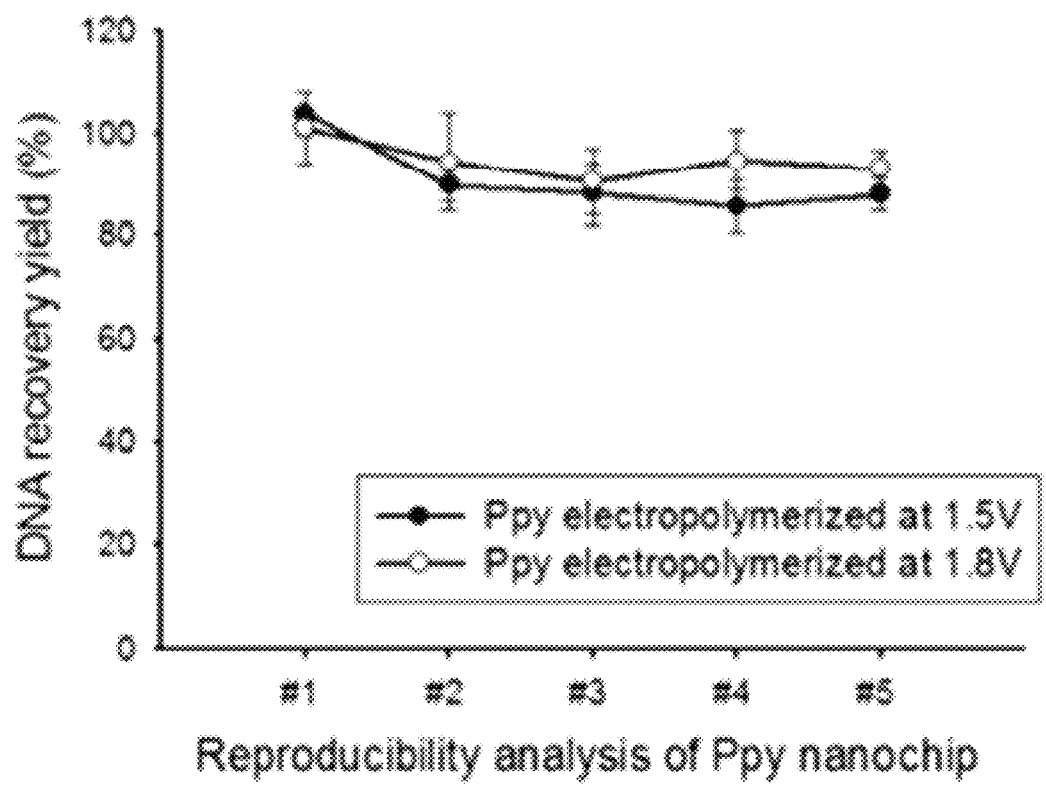
FIG. 11B illustrates results of cfDNA isolation repeatedly performed using a Ppy nanochip structure of the present invention.
Figure 11C:
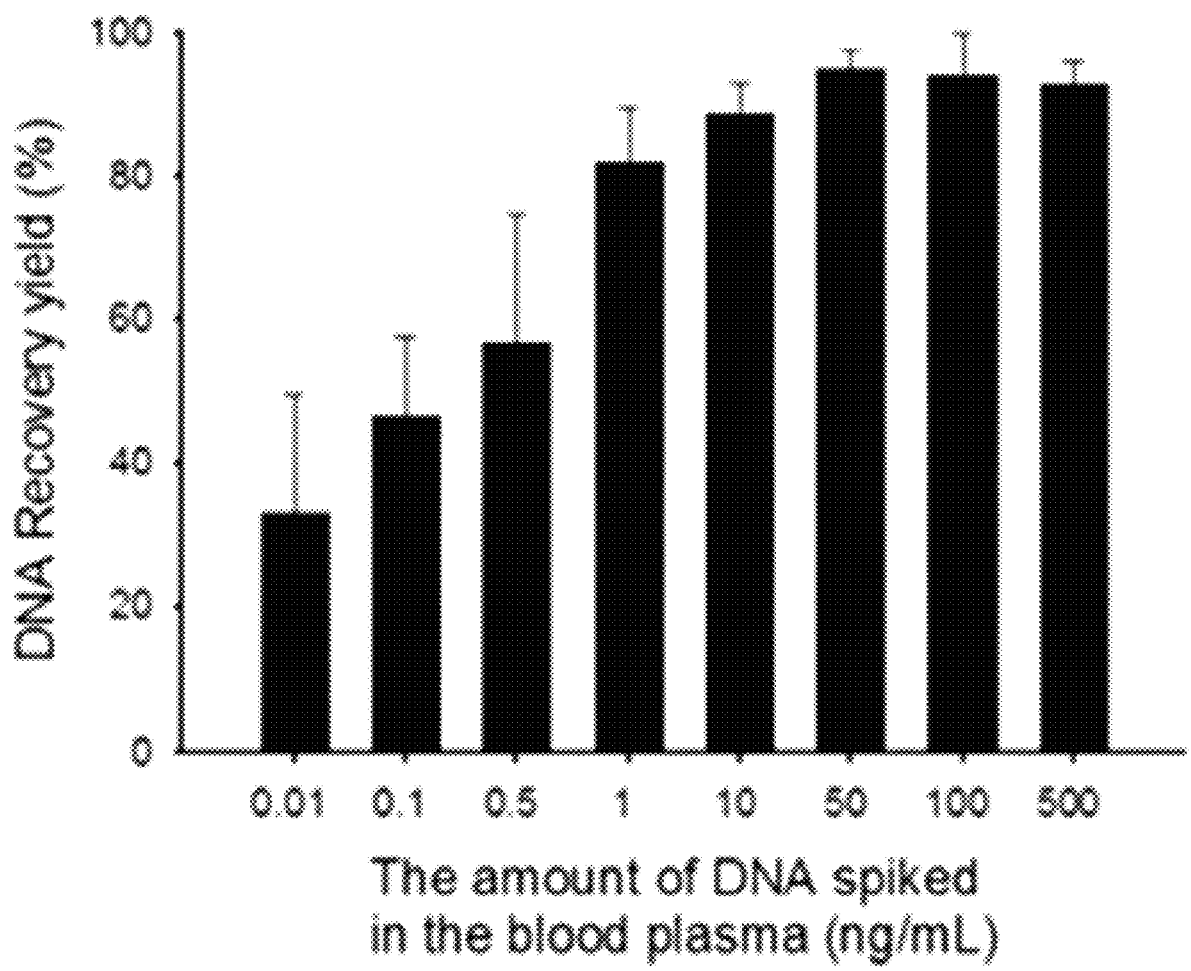
FIG. 11C illustrates evaluation results of concentration-based attachment and isolation ability to cfDNA using a Ppy nanochip structure of the present invention.

In addition, as illustrated in FIG. 11B, it was confirmed that, as a result of repetitive cfDNA isolation using the Ppy nanochip structure, the Ppy nanochip structure was spontaneously reduced at voltages of 1.5 V and 1.8 V, and thus DNA was isolated. In addition, the attachment and isolation ability of the Ppy structure was evaluated by varying the concentration of cfDNA, as illustrated in FIG. 11C. As a result, it was confirmed that the attachment and isolation efficiency increased with increasing concentration of cfDNA concentration.

Example 6. Evaluation of Attachment/Isolation Ability to cfDNA Using Various Isolation Techniques and Various-Size DNA To evaluate cfDNA attachment/isolation ability of various conventional isolation techniques and the polypyrrole nanochip structure of the present invention, DNA was spiked into a human plasma at a concentration of 250 ng/ml (low-range (10 to 100 bp), middle-range (100 bp to 2 kb), and high-range (3.5 to 21 kb)). As conventional techniques, a Ppy nanochip structure, a Qiagen kit, a Triton/Heat/Phenol (THP) protocol, and magnetic beads were used.

Cell-free DNA was extracted from plasma using a QIAamp Circulating Nucleic Acid Kit (Qiagen) and an Agencourt Genfind V2 magnetic bead genomicDNA isolation kit (Beckman Coulter) according to the manufacturer's instructions. For the Triton/Heat/Phenol (THP) method, 200 mL of plasma was mixed with TritonX-100 and heated at 98° C. for 5 min. An equal volume of phenol-chloroform-isoamyl alcohol (25:24:1, pH 8.0) (Biosesang) was added to the resulting samples and centrifuged at 14,000 rpm for 10 min. The aqueous phase was then incubated with 2.5 times the volume of 100% ethanol and ⅒ of the volume of 2 M sodium acetate (NaOAc) at −80° C. for 1 h to induce the precipitation a DNA pellet. The isolated DNA samples were suspended in 70% ethanol, dried at room temperature, and finally eluted with 20 mL of NFW. The resulting cfDNA was electrophoresed on 2% agarose gel and stained with ethidium bromide for visualization using a UV transilluminator. In addition, as described in Example 1-2, various-size DNA samples were used.

Figure 12A:
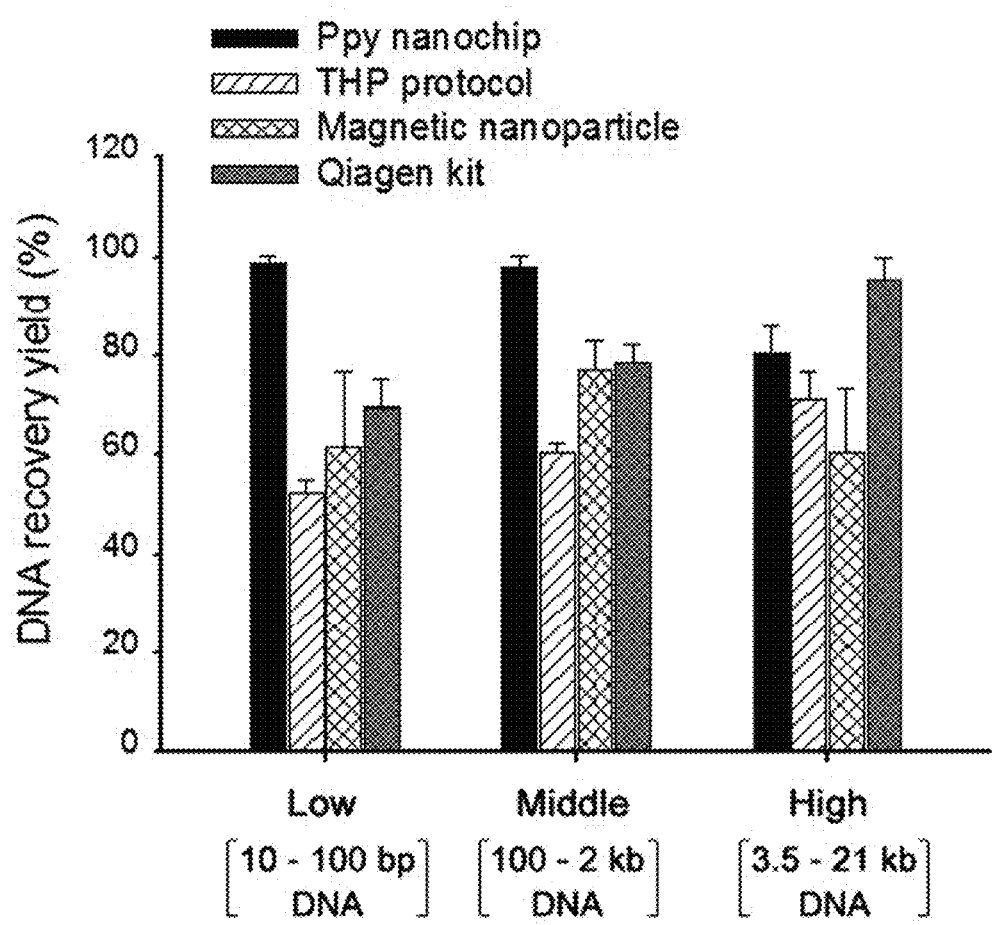
FIG. 12A illustrates, after spiking various-size DNA into the blood plasma of a normal person, attachment and isolation ability of a Ppy nanochip structure to ctDNA.
Figure 12B:
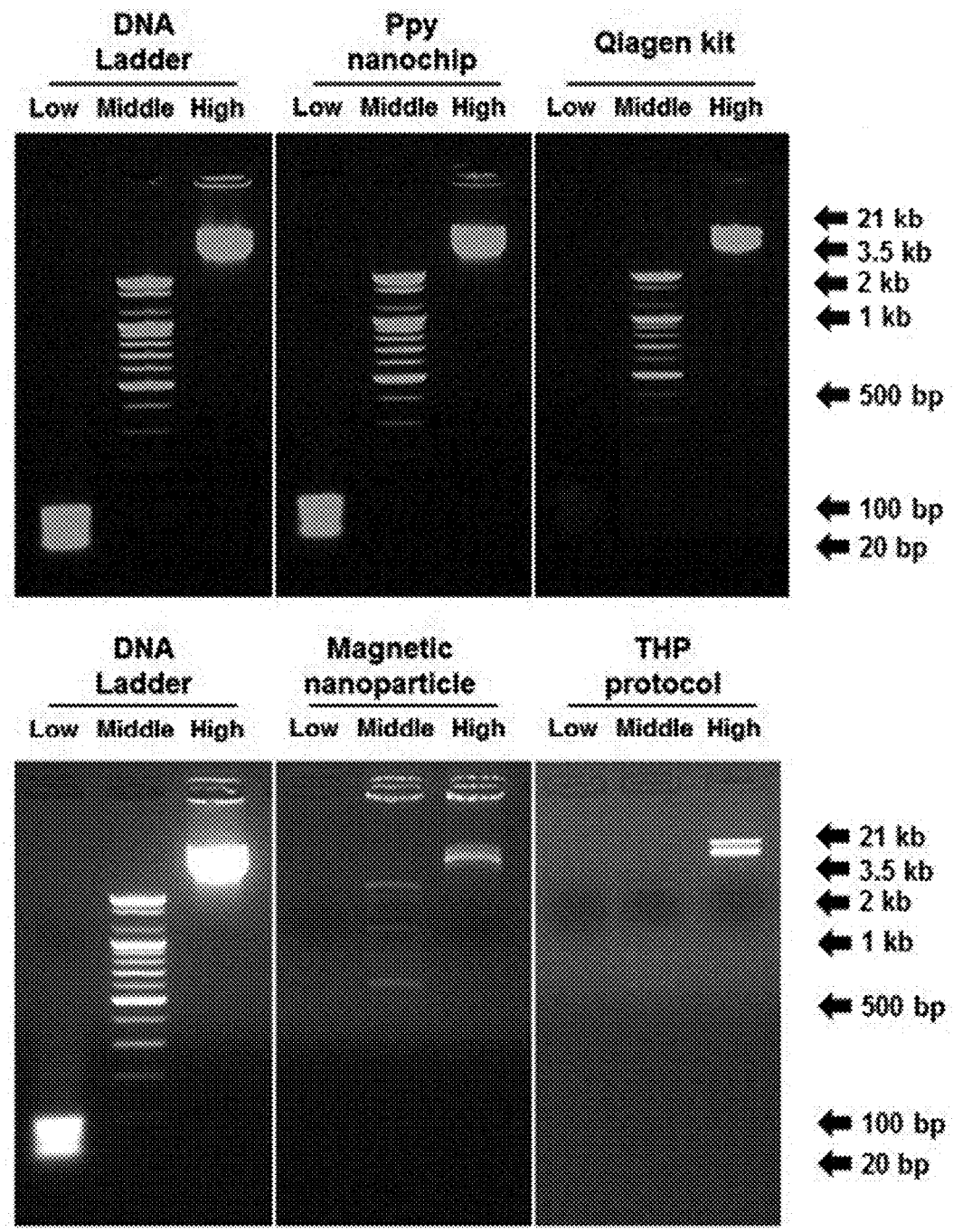
FIG. 12B illustrates comparison results, by electrophoresis, of efficiencies of various conventional cfDNA isolation technologies and a Ppy structure nanochip.

As illustrated in FIG. 12A, after spiking various-size DNA into the plasma from a normal person, attachment and isolation ability to ctDNA was evaluated using the various conventional cfDNA isolation techniques and the Ppy nanochip structure of the present invention. As a result, it was confirmed that the Ppy nanochip structure exhibited the highest efficiency of 95% in isolating short DNA fragments. Similarly, as illustrated in FIG. 12B, efficiency of the conventional various cfDNA isolation techniques and efficiency of the Ppy nanochip structure of the present invention were compared. As a result, the Ppy nanochip structure exhibited the highest efficiency in isolating the shortest DNA fragments.

Example 7. Evaluation of cfDNA Present in Blood from Lung Cancer Patient Using Polypyrrole Nanochip Structure To perform an additional experiment for the clinical utility of the polypyrrole nanochip structure, cfDNA was extracted from each of plasma samples from a healthy donor and a lung cancer patient, and the yields of the extracted cfDNA were measured and compared to each other. Cell lines used in the present invention were purchased from the American Type Culture Collection (ATCC). Mesenchymal stem cell (MSC) lines were cultured in Mesenchymal Stem Cell Basal Medium supplemented with an MSC Growth kit (ATCC, Manassas, Va., USA), and lung cancer cell lines (H1975 and HCC2279) were cultured in Roswell Park Memorial Institute (RPMI)-1640 medium (GE Healthcare Life Sciences, Chicago, Ill., USA) supplemented with 10% fetal bovine serum (FBS). H1975 cell lines contain epidermal growth factor receptor gene (EGFR) L858R point mutations in exons 21, whereas HCC2279 contains an EGFR deletion (D746e750) in exon 19. In the present invention, DNA mutation was analyzed using the digital PCR described in Examples 1-6 and 1-7. Genomic DNA was isolated using a QIAamp DNA Mini Kit (Qiagen, Hilden, Germany), and DNA concentration was measured using a NanoDrop ND-1000 spectrophotometer (Thermo Scientific). All primers and probes of EGFR L858R were synthesized in Bioneer, Korea. Sequences of used EGFR L858R are as follows.

TABLE 3

| Primer Name | Primer sequence (5' → 3') | |
|---|---|---|
| EGFR L858R forward primer | 5'-GCAGCATGTCAAGATCACA GATT-3' | SEQ ID NO: 9 |
| EGFR L858R reverse primer | 5'-CCTCCTTCTGCATGGTATT CTTTCT-3' | SEQ ID NO: 10 |
| probe | 5'-FAM-AGTTTGGCCAGCCCA A-BHQ-3' | SEQ ID NO: 11 |

Figure 13:
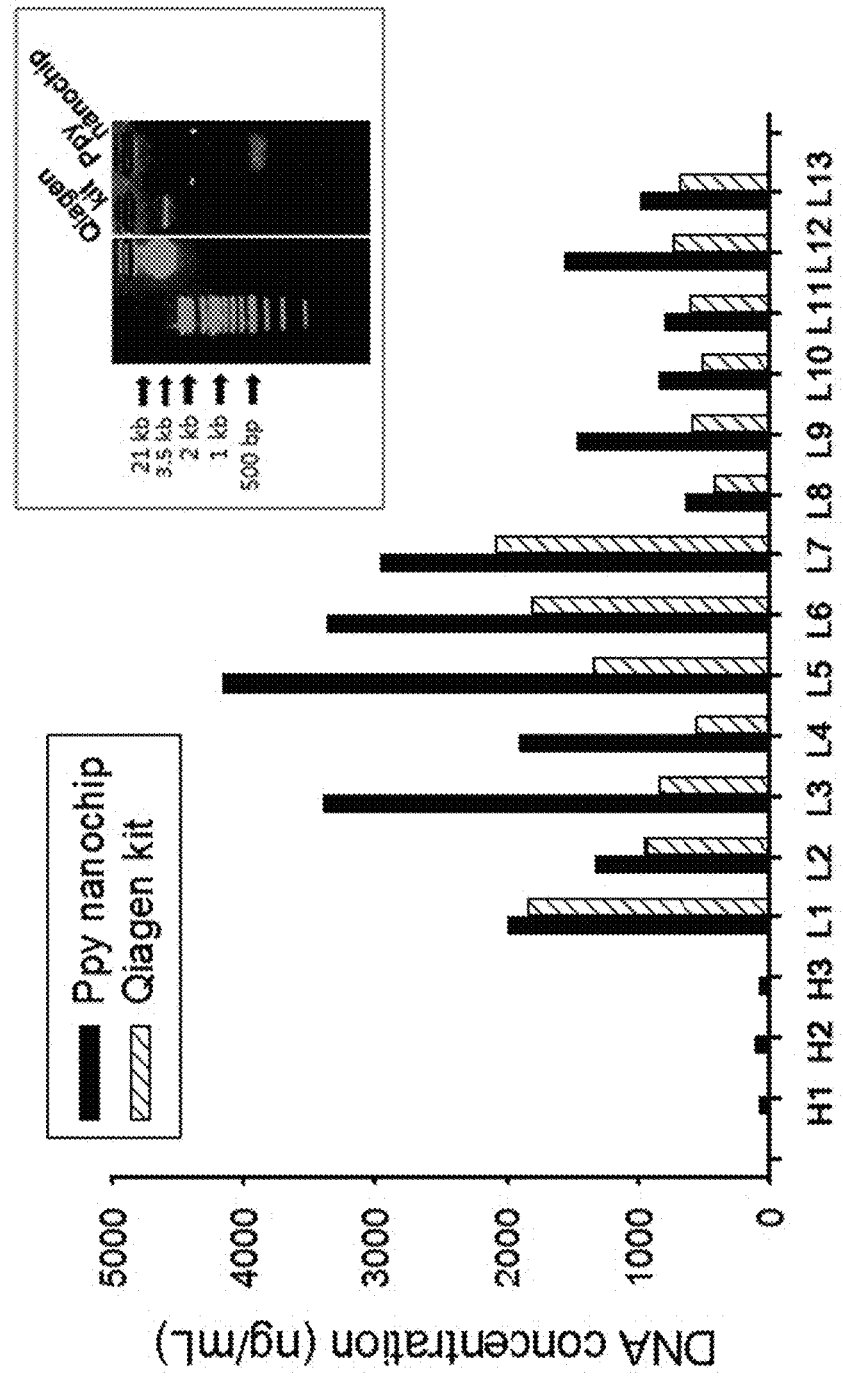
FIG. 13 illustrates, after isolating cfDNA present in the blood of each of a normal person and a lung cancer patient using each of a Ppy nanochip structure of the present invention and a commercially available Qiagen kit, comparison results of the concentrations of the isolated cfDNA.

As a result, as illustrated in FIG. 13, cfDNA present in blood from each of a normal person and a lung cancer patient was isolated using each of Ppy nanochip structure of the present invention and the commercially available Qiagen kit, and then the concentrations of the isolated cfDNAs were compared. As a result, it was confirmed that the Ppy nanochip structure of the present invention had much higher efficiency in detecting cfDNA.

Figure 14A:
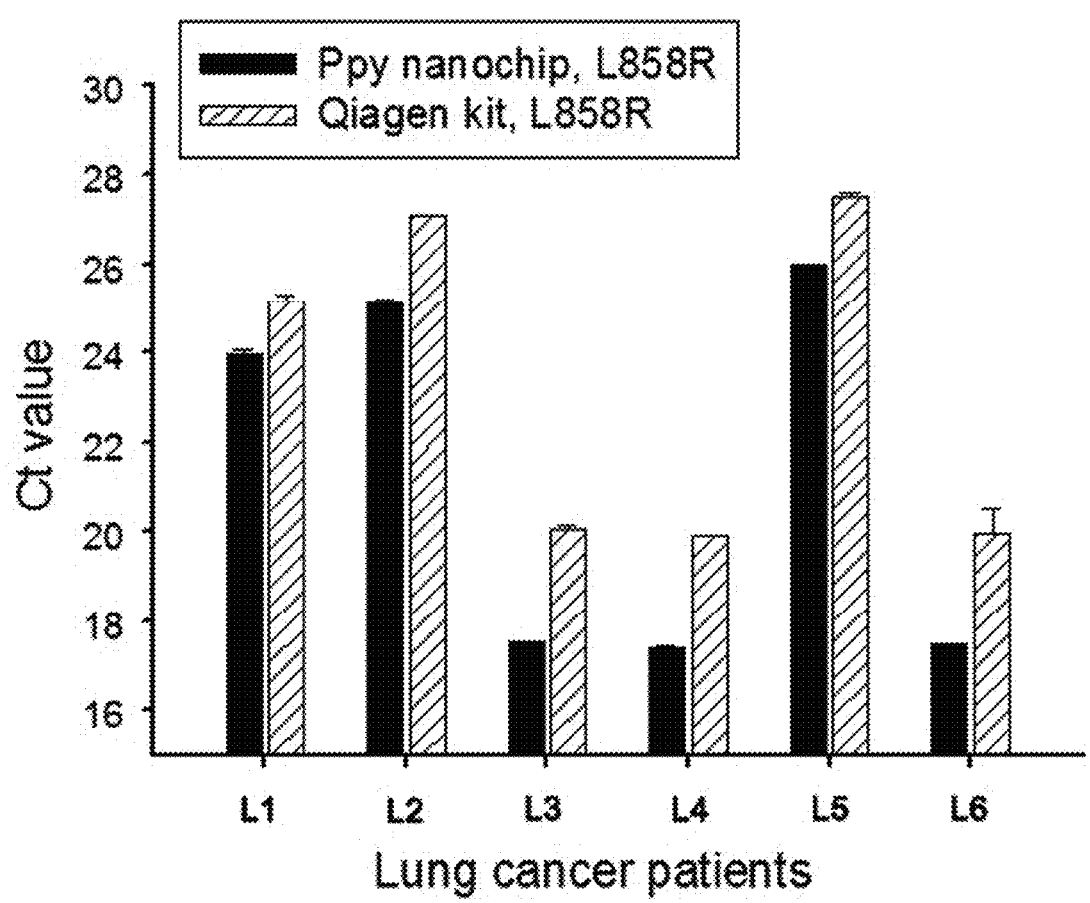
FIGS. 14A and 14B illustrate, after isolating cfDNA present in the blood of a lung cancer patient using each of a Ppy structure nanochip of the present invention and a commercially available Qiagen kit, evaluation results of modification efficiency of an EGFR exon 21 L858R gene through real-time PCR.
Figure 14B:
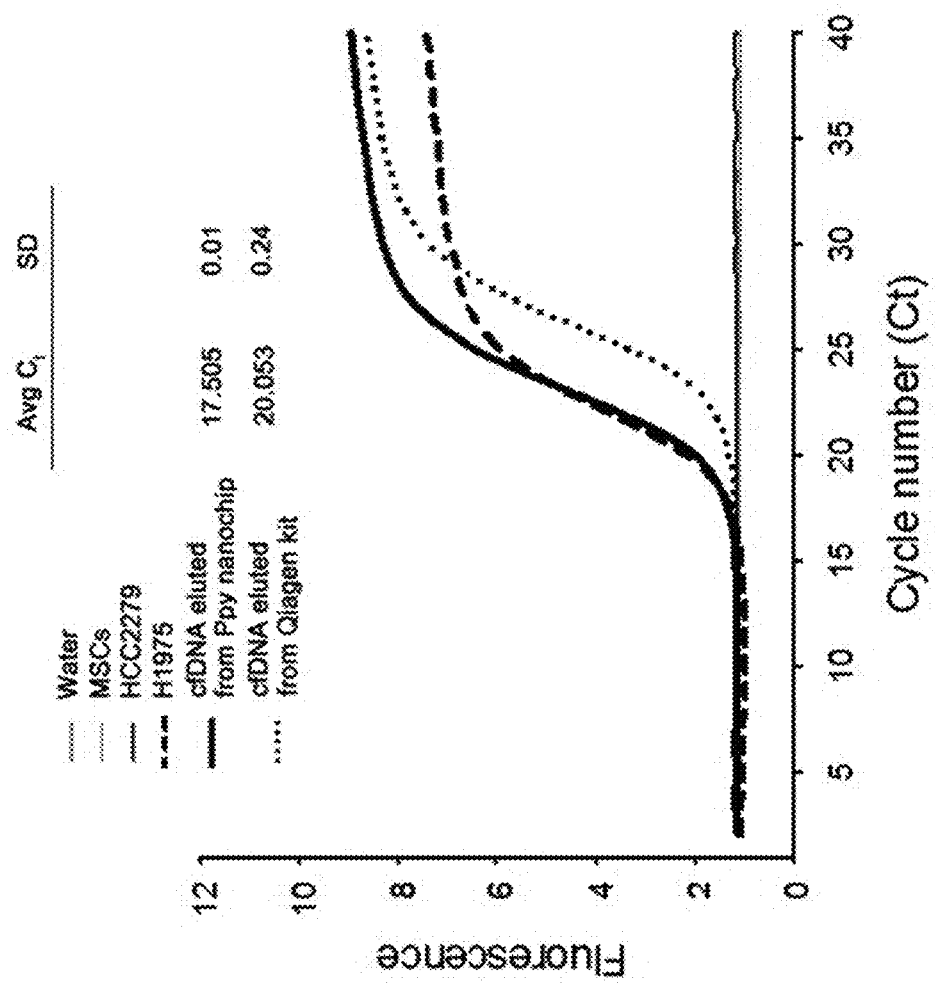

In addition, as illustrated in FIGS. 14A and 14B, cfDNA present in blood from a lung cancer patient was isolated using each of the Ppy nanochip structure of the present invention and the commercially available Qiagen kit, and then was amplified using real-time PCR, followed by investigating EGFR exon 21 L858R gene mutation. As a result, superior performance of the polypyrrole nanochip structure of the present invention was confirmed.

Since the structure for detecting cell-free DNA according to the present invention includes an electrochemically surface-modified conductive polymer and polymer may be positively or negatively charged, the structure allows easy attachment and isolation of cell-free DNA including circulating tumor DNA (ctDNA) and the like and provides remarkably increased detection efficiency. Finally, effectively detecting or isolating circulating tumor DNA by an electric signal is anticipated to be very useful in diagnosing the onset of cancer and predicting the diagnosis thereof.

Although certain parts of the contents of the present invention have been described in detail above, it will be obvious to those skilled in the art that such particulars are only provided as preferred embodiments and the present invention is not intended to be limited to the embodiments. Accordingly, it will be obvious that the scope of the present invention is not limited to the described particulars. Therefore, the substantial scope of the present invention will be defined by the accompanying Claims and the equivalents thereof.

INDUSTRIAL APPLICATION

The structure for detecting and isolating cell-free DNA according to the present invention allows easy attachment and isolation of cell-free DNA including circulating tumor DNA (ctDNA) and the like and provides remarkably increased detection efficiency. Finally, effectively detecting or isolating circulating tumor DNA by an electric signal is anticipated to be very useful in diagnosing the onset of cancer and predicting the diagnosis thereof.

What is claimed is:

1. A method of isolating cell-free DNA (cfDNA) from a biological sample containing the cfDNA, the method comprising:
   positively charging a surface of nanostructure;
   treating the nanostructure with the biological sample so that the cfDNA is attached to the nanostructure; and
   isolating the cfDNA by releasing the cfDNA from the nanostructure by applying an electric signal,
   wherein the nanostructure is only electrochemically modified and the nanostructure is a nanochip, a nanodot, a nanorod, or a nanowire,
   wherein the nanostructure consists of an electrode and a conductive polymer coating the electrode, and
   wherein the nanostructure has surface roughness and thereby a ratio of a volumetric area relative to a surface increases.

2. The method according to claim 1, wherein the biological sample is selected from the group consisting of a blood sample, a bone marrow sample, a pleural fluid sample, a peritoneal fluid sample, a spinal fluid sample, a urine sample, and a saliva sample.

3. The method according to claim 2, wherein the biological sample is a blood sample.

4. The method according to claim 1, wherein the cfDNA is attached to the nanostructure by applying an electric signal at 0.8 to 1.2 V for 20 to 40 seconds.

5. The method according to claim 1, wherein the cfDNA is released from the nanostructure by applying an electric signal at −1.3 to −1.0 V for 4 to 6 minutes.

6. The method according to claim 1, wherein the cell-free DNA is circulating tumor DNA.

7. The method according to claim 1, wherein the conductive polymer is polypyrrole.

* * * * *